US006927283B2

(12) United States Patent
Fox et al.

(10) Patent No.: US 6,927,283 B2
(45) Date of Patent: Aug. 9, 2005

(54) MODIFIED ACYL CARRIER PROTEINS

(75) Inventors: Brian G. Fox, Madison, WI (US); Jeffrey A. Haas, Davis, CA (US)

(73) Assignee: Wisconsin Alumni Research Foundation, Madison, WI (US)

( * ) Notice: Subject to any disclaimer, the term of this patent is extended or adjusted under 35 U.S.C. 154(b) by 151 days.

(21) Appl. No.: 10/001,453

(22) Filed: Oct. 22, 2001

(65) Prior Publication Data

US 2005/0118668 A1 Jun. 2, 2005

(51) Int. Cl.⁷ .......................... C07K 14/00; C07K 1/00; C12P 21/06; C12N 1/20; C12N 15/00
(52) U.S. Cl. .................. 530/402; 435/69.1; 435/252.3; 435/320.1; 536/23.1
(58) Field of Search .................... 530/402; 435/69.1, 435/252.3, 320.1; 536/23.1, 252.3, 320.1

(56) References Cited

PUBLICATIONS

McAllister et al. Abstracts of the Interscience Conference on Antimicrobial Agents and Chemotherapy, (2000) vol. 40, pp. 225. print. Meeting Info.: 40th Interscience Conference on Antimicrobial Agents and Chemotherapy. Toronto, Ontario, Canada. Sep.*
Dawson et al. [Data for biochemical research, 3rd edition, 1986, see reagents for protein modifications, pp. 388–393].*
Hass et al. Protein Expression and Purification vol. 20, Issue 2, Nov. 2000, pp. 274–284.*
Abita, J. P., Lazdunski, M. & Ailhaud, G. (1971). Structure–function relationships of the acyl–carrier protein of *Escherichia coli*. *Eur. J. Biochem* 23, 412–420.
Aristidou, A. A., San, K. & Bennett, G. N. (1999). Improvement of biomass yield and recombinant gene expression in *Escherichia coli* by using fructose as the primary carbon source. *Biotechnol. Prog.* 15, 140–145.
Baldwin, J. E., Bird, J. W., Field, R. A., O'Callaghan, N. M., Schofield, C. J. & Willis, A. C. (1991). Isolation and partial characterisation of ACV synthetase from *Cephalosporium acremonium* and *Streptomyces calvuligerus:* Evidence for the presence of phosphopantothenate in ACV synthetase. *J. Antibiot. (Tokyo)* 44, 241–248.
Bradford, M. M. (1976). A rapid and sensitive method for the quantitation of microgram quantities of protein utilizing the principle of protein–dye binding. *Anal. Biochem.* 72, 248–254.
Broadwater, J. A., Ai, J., Loehr, T. M., Sanders–Loehr, J. & Fox, B. G. (1998). Peroxodiferric intermediate of stearoyl–l–acyl carrier protein $\Delta^9$ desaturase: oxidase reactivity during single turnover and implications for the machanism of desaturation. *Biochemistry* 37, 14664–14671.
Broadwater, J. A., Achim, C., Münck, E. & Fox, B. G. (1991). Mössbauer studies of the formation and reactivity of a quasi–stable peroxo intermediate of stearoyl–acyl carrier protein $\Delta^9$ –desaturase. *Biochemistry* 38, 12197–12204.

Broadwater, J. A. & Fox, B. G. (1999). Spinach holo–acyl carrier protein: overproduction and phosphopantetheinylation in *Escherichia coli* BL21(DE3), in vitro, acylation, and enzymatic desaturation of histidine–tagged isoform I. *Protein Express. Purif.* 15, 314–326.
Ellman, G. L. (1959). Tissue sulfhydryl groups. *Arch. Biochem. Biophys.* 82, 70–77.
Fox, B. G., Shanklin, J., Somerville, C. & Münck, E. (1993). Stearoyl–acyl carrier protein $\Delta D^9$ desaturase from *Ricinus communis* is a diiron–oxo protein. *Proc. Natl. Acad. Sci., USA* 90, 2486–2490.
Fox, B. G., Shanklin, J., AI, J., Loehr, T. M. & Sanders–Loehr, J. (1994). Resonance Raman evidence for an Fe–O–Fe center in stearoyl–ACP desaturase. Primary sequence identity with other diiron–oxo proteins. *Biochemistry* 43, 12776–12786.
Fox, B. G. (1997). Catalysis by non–heme iron. In *Comprehensive Biological Catalysis* (Sinnott, M., ed.), pp. 261–348. Academic Press, London.
Garsin, D.A., Sifri, C.D., Mylonakis, E., Qin, X., Singh, K.V., Murray, B.E., Calderwood, S.B., and Ausubel, F.M. (2001) *Proceedings of the National Academy of Sciences USA* 98, 10892–10897.
Haas, J. A. & Fox, B. G. (1999). Role of hydrophobic partitioning in substrate selectivity and turnover of the *Ricinus communis* stearoyl–ACP $\Delta^9$ desaturase. *Biochemistry* 38, 12833–12840.
Hill, R. B., Mackenzie, K. R., Fianafan, J. M., Cronan, J. E. & Prestegard, J. H. (1995). Overexpression, purification, and characterization of *Escherichia coli* acyl carrier protein and two mutant proteins. *Protein Express. Purif.* 6, 394–400.
Hoang, T.T., Ma, Y., Stern, R.J., McNeil, M.R., and Schweuzer, H.P. (1999) *Gene* 237, 361–371.
Keating, D. H., Carey, M. R. & Cronan, J. E., Jr. (1995). The unmodified (apo) form of *Escherichia coli* acyl carrier protein is a potent inhibitor of cell growth. *J. Biol. Chem.* 270, 22229–22235.
Kenner, A. (1971). Fluorescent derivatives of nitrotyrosine. Model compounds for fluorescent reporter groups in proteins. *Biochemistry* 10, 545–550.
Kim, Y. & Prestegard, J. H. (1990). Refinement of the NMR structures for acyl carrier protein with scalar coupling data. *Proteins: Struct. Funct. Genet.* 8, 377–385.
Kraulis, P. J. (1991). Molscript: a program to produce both detailed and schematic plots of protein structures. *J. Appl. Crystal.* 24, 946–950.

(Continued)

*Primary Examiner*—Tekchand Saidha
(74) *Attorney, Agent, or Firm*—Joseph T. Leone, Esq.; DeWitt Ross & Stevens S.C.

(57) ABSTRACT

Disclosed are apo-, holo-, and acylated-acyl carrier proteins modified to have a non-radioactive label covalently bonded to a modified tyrosine residue within the acyl carrier protein. Also disclosed are methods of using the labeled acyl carrier proteins to investigate reaction involving or mediated by acyl carrier proteins. Also disclosed are kits containing the non-radioactively-labeled acyl carrier proteins.

35 Claims, 10 Drawing Sheets

OTHER PUBLICATIONS

Lawson, D. M., Derewenda, U., Serre, L., Ferri, S., Szittner, R., Wei, Y., Meighan, E. A. & Derewenda, Z. S. (1994). Structure of a myristoyl–ACP–specific thioesterase from *Vibrio harveyi. Biochemistry* 33, 9382–9388.

Lindqvist, Y., Huang, W., Schneider, G. & Shanklin, J. (1996). Crystal structure of stearoyl–acyl carrier protein $\Delta^9$ desaturase from castor seed and its relationship to other diiron proteins. *Embo J.* 15, 4081–4092.

Magnuson, K., Jackowski, S., Rock, C. O. & Cronan, J. E., Jr. (1993). Regulation of fatty acid biosynthesis in *Escherichia coli. Annu. Rev. Microbiol.* 57, 522–542.

Miller, M.B., and Bassler, B.L. (2001), Annual Review of Microbiology. 55, 165–199.

Prescott, D. J. & Vagelos, P. R. (1972). Acyl carrier protein. *Adv. Enzy. and Rel. Areas of Mol. Bio.* 36, 269–311.

Rock, C. O. & Garwin, J. L. (1979). Preparative enzymatic synthesis and hydrophobic chromatography of acyl–acyl carrier protein. *J. Biol. Chem.* 254, 7123–7128.

Rusnak, F., Sakaitani, M., Drueckhammer, D., Reichert, J. & Walsh, C. T. (1991). Biosynthesis of the *Escherichia coli* siderophore enterobactin: Sequence of the *entF* gene, expression and purification of EntF, and analysis of covalent phosphopantetheine. *Biochemistry* 30, 2916–2927.

Sambrook, J., Fritsch, E. F. & Maniatis, T., Eds. (1989). *Molecular Cloning. A Laboratory Manual.* 2nd edit. Cold Spring Harbor Laboratory Press. Cold Spring Harbor, NY. (Copy Not Provided).

Schagger, H. T Von Jagow, G. (1987). Tricine–sodium dodecyl sulfate–polyacrylamide gel electrophoresis for the separation of proteins in the range from 1 to 100 kDa. *Anal. Biochem.* 166, 368–379.

Shanklin, J. & Cahoon, E. B. (1998). Desaturation and related modifications of fatty acids. *Annu. Rev. Plant Physiol. Plant Mol. Biol.* 49, 611–641.

Singh, P.K., Schaefer, A.L., Parsek, M.R., Moninger, T.O., Welsh, M.J., and Greenberg, E.P. (2000) "The Establishment of Biofilms." *Nature* 407, 762–764.

Sokolovsky, M., Riordan, J. F. & Vallee, B. L. (1966). Tetranitromethane. A reagent for the nitration of tyrosyl residues in proteins. *Biochemistry* 5, 3582–3588.

Sokolovsky, M., Riordan, J. F. & Vallee, B. L. (1967). Conversion of 3–nitrotyrosine to 3–aminotyrosine in peptides and proteins. *Biochem. Biophys. Res. Commun.* 27, 20–25.

Sperandio, V., Torres, A.G., Giron, J.A., and Kaper, J.B. (2001) *Journal of Bacteriology* 183, 5187–5197).

Studts, J. M. & Fox, B. G. (1999). Application of fed–batch fermentation to the preparation of isotopically labeled or selenomethionyl–labeled proteins, *Protein Express. Purif.* 16, 109–119.

Summers, R. G., Ali, A., Shen, B., Wessel, W. A. & Hutchinson, C. R. (1995). Malonyl–coenzyme A:acyl carrier protein acyl–transferase of *Streptomyces glaucescens:* A possible link between fatty acid and polyketide biosynthesis, *biochemistry* 34, 9389–9402.

Yang, Y., Broaadwater J. A., Pulver, S. C., Fox, B. G. & Solomom, E. I. (1999). Circular dichroism and magnetic circular dichroism studies of the reduced binuclear non–heme iron site of stearoyl–ACP $\Delta^9$ desaturase: substrate binding and comparison to ribonucleotide reductase. *J. Am. Chem. Soc.* 121, 2770–2783.

Molecular Probes, FluoReporter®Rhodamine Red™–X Protein Labeling Kit (F–6161), Product Information, Revised Mar. 7, 2001, 4 pages.

Molecular Probes, FluoReporter®Texa Red™–X Protein Labeling Kit (F–6162), Product Information, Revised Jan. 23, 2001, 3 pages.

Molecular Probes, FluoReporter® Tetramethylrhodamine Protein Labeling Kit (F–6163), Product Information, Revised Feb. 12, 2001, 3 pages.

Molecular Probes, FluoReporter®Fluorescein–EX Protein Labeling Kit (F–6433), Product Information, Revised Mar. 9, 2001, 4 pages.

Molecular Probes, FluoReporter® FITC Protein Labeling Kit (F–6434), Product Information, Revised Mar. 13, 2001.

Worsham et al., 2003, Amino Acid Residues of *Escherichia coli* Acyl Carrier Protein Involved in Heterologous Protein Interactions, *Biochemistry,* 42:167–176.

\* cited by examiner

SEQUENCE LISTING

<160> NUMBER OF SEQ ID NOS: 2

<210> SEQ ID NO 1
<211> LENGTH: 32
<212> TYPE: DNA
<213> ORGANISM: Artificial Sequence
<220> FEATURE:
<223> OTHER INFORMATION: PCR Primer

<400> SEQUENCE: 1
ccgcacatat gagcaccatc gaagaacgtg tg                32

<210> SEQ ID NO 2
<211> LENGTH: 33
<212> TYPE: DNA
<213> ORGANISM: Artificial Sequence
<220> FEATURE:
<223> OTHER INFORMATION: PCR Primer

<400> SEQUENCE: 2
caatactcga gttacgcctg gtggccgttg atg               33

US 6,927,283 B2

MODIFIED ACYL CARRIER PROTEINS

This invention was made with United States government support awarded by the following agencies: NIH GM50853. The United States has certain rights in this invention.

FIELD OF THE INVENTION

The invention is directed to acyl carrier proteins (ACPs) modified to include a label such as a fluorophore or chromophore. The ACPs so modified function in exactly the same fashion as unmodified ACPs, and therefore have utility in investigating reactions mediated by or involving ACPs. The invention is also directed to a synthetic method for fabricating the modified ACPs.

BACKGROUND

Acyl carrier proteins (ACPs) are small (~8 to 10 kDa) acidic proteins that contain a 4'-phosphopantetheine prosthetic group. This prosthetic group is attached to a conserved serine residue in apo-ACP by holo-ACP synthase. (That is, apo-ACP is converted to holo-ACP by addition of the prosthetic group, a reaction catalyzed by holo-ACP synthase.) In -holo-ACP, the prosthetic group provides a free thiol group that is required for ACP to function in a variety of biosynthetic pathways including de novo biosynthesis of fatty acids,[1] depsipeptides,[2] peptides,[3] polyketides,[4] the posttranslational acylation of proteins,[5] bacterial quorum sensing,[32] the synthesis of intercellular signalling molecules,[33] the establishment of biofilms,[34] and conversion to virulence.[35, 36]

Acyl-ACPs are also substrates for the soluble desaturases found in the plastid organelles of plants and photoauxotrophic *Euglena*.[6] The stearoyl-ACP $\Delta^9$ desaturase ($\Delta$9D) from *Ricinus communis* is the best characterized member of this enzyme family.[7] The $\Delta$9D desaturase catalyzes the NADPH- and $O_2$-dependent insertion of a cis-double bond at the C9 position of 18:0-ACP to form 18:1-ACP. Non-heme diiron centers found in each subunit of the homodimeric $\Delta$9D (8–10) are utilized for the $O_2$ activation steps of catalysis.

Recent studies have revealed the importance of protein-protein interactions between acyl-ACP and $\Delta$9D in the determination of catalytic selectivity,[11] the perturbation of the ligation environment of the diiron center,[12] and the accumulation of a quasi-stable peroxodiiron(III) species.[13, 14]

There is, however, an acute need to elucidate these interactions in greater detail. Further biophysical characterization of the protein-protein interactions involved in these catalytic phenomena would be facilitated by the availability of selective probes for complex formation. Because neither acyl-ACP, nor $\Delta$9D, nor other protein partners that interact with ACP in the above-mentioned biological processes exhibits chromophoric features suitable for these studies, another tack must be taken. The present invention addresses this long-felt need by providing a method to synthesize suitably-derivatized forms of acyl-ACP that allows non-radioactive monitoring of reactions involving ACP. Thus, the present invention is directed to ACPs with a site-specific chromophoric or fluorophoric modification. The labeled ACP can be used a probe and includes the appropriate fatty acyl derivative required for subsequent catalytic reactions.

SUMMARY OF THE INVENTION

A first embodiment of the invention is directed to a labeled acyl carrier protein. The labeled protein comprises an acyl carrier protein (apo-, holo-, or acylated ACP) having bonded thereto a non-radioactive label. The labeled ACP reacts substantially identically to non-labeled ACP in chemical and enzymatic reaction.

The preferred first embodiment is a labeled acyl carrier protein wherein the acyl carrier protein has at least one tyrosine residue, and more preferably still has only one tyrosine residue. Here, the tyrosine residue is modified to include a non-radioactive label covalently bonded thereto. The label is preferably a fluorophore. In ACP from *E. coli*, there is only a single unique tyrosine residue at position Y71 and the label is attached to this unique tyrosine.

A second embodiment of the invention is a kit for investigating reactions involving acyl carrier proteins. The kit comprises a container having disposed therein an acyl carrier protein (apo-, holo-, or acylated ACP) having bonded thereto a non-radioactive label. As in the first embodiment, it is preferred that the acyl carrier protein have at least one tyrosine residue, and most preferred that the acyl carrier protein have only one tyrosine residue.

A third embodiment of the invention is a method of making a holo-acyl carrier protein having a non-radioactive label affixed thereto. The method comprises first reacting an apo-ACP having at least one tyrosine residue with a chemical reagent capable of covalently bonding an amino moiety to the tyrosine residue. This yields an apo-ACP having an amino-modified tyrosine moiety. A non-radioactive label is then covalently bonded to the amino-modified tyrosine moiety, thereby yielding an apo-ACP having a non-radioactive label covalently bonded thereto. The apo-acyl carrier protein having the label attached is then reacted with a holo-acyl carrier protein synthase under time and conditions sufficient to convert the apo-acyl carrier protein to a holo-acyl carrier protein having a non-radioactive label affixed thereto.

A third embodiment of the invention is a method of making an acylated-ACP having a non-radioactive label affixed thereto. Here, the method comprises all of the steps listed in the immediately preceding paragraph, followed by an additional step of reacting the holo-acyl carrier so formed with an acyl-ACP synthetase under time and conditions sufficient to convert the holo-acyl carrier protein to an acylated-ACP having a non-radioactive label affixed thereto.

The utility of the present invention is manifest. ACPs play many different biological roles. By providing a non-radioactively labeled version of these important proteins, their interactions can be investigated in greater detail, with greater ease, and with greater precision than with, for example, $^{32}$P-labeled ACPs.

BRIEF DESCRIPTION OF THE DRAWINGS

FIG. 1A: map of plasmid pEACP-2 used for expression of acpP. FIG. 1B: map of plasmid pBHF-5 used for expression of acpP. FIG. 1C map of plasmid pBHF-1 used for coexpression of acpP and acpS.

FIG. 2A: absorbance spectrum in 50 mM MES, pH 5.5 (dashed-line) or 50 mM Tris pH 8.8 (solid-line). FIG. 2B. ESI-MS showing nitroTyr-ACP without (8555 Da) and with (8686 Da) N-terminal Met. The minor peak at 8575 Da is likely a $Ca^{2+}$ adduct of nitroTyr-ACP.

FIG. 3B: ESI-MS showing aminoTyr-ACP without (8524 Da) and with (8655 Da) N-terminal Met. Minor peaks at 8544 and 8564 Da are likely $Ca^{2+}$ adducts of aminoTyr-ACP. The peak at 8604 Da is probably dinitro-ACP.

FIGS. 4A and 4B. Characterization of purified dansylaminoTyr-ACP. FIG. 4A: absorbance spectrum in 25 mM succinate, pH 5.0. FIG. 4B: ESI-MS showing dansylaminoTyr-ACP (8757 Da), aminoTyr-ACP (8524 Da), and dansylaminoTyr-ACP with N-terminal Met (8889 Da). The peak at 8780 Da is likely a $Na^{30}$ adduct of dansylaminoTyr-ACP.

FIG. 5A: Coomassie Blue-stained gel containing molecular mass standards, lane 1; dansylaminoTyr-ACP, lane 2; 18:0-dansylaminoTyr-ACP, lane 3. FIG. 5B: Photograph of the gel from FIG. 5A placed on a light box under 300 nm reflected light prior to Coomassie staining; dansylaminoTyr-ACP, lane 1; 18:0-dansylaminoTyr-ACP, lane 2.

FIG. 6A: Time-dependent accumulation of 18:1 at a fixed initial 18:0-dansylaminoTyr-ACP (2 µM). (■) Nanomoles of 18:1 produced. The solid line is a linear least-squares fit ($r^2$=0.99) whose slope is the initial desaturation rate, $v_o$. FIG. 6B: Dependence of $v_o$ as determined in FIG. 6A on the concentration of 18:0-dansylaminoTyr-ACP. (■) Measured $v_o$ ($min^{-1}$). The solid line is a nonlinear least squares fit ($r^2$=0.98) to the Michaelis-Menten equation, $v_o = k_{cat} \times \{S\}/(K_M + \{S\})$.

FIG. 7A depicts the results of fluorescence anisotropy-detected titration of 0.85 µM 18:0-dACP with Δ9D showing a 1:1 stoichiometry of binding. The solid lines are linear least squares fits to the data. FIG. 7B: Titration data from FIG. 7A and results of non-linear least-squares fitting using equation 2 as described in Example 13.

FIG. 8B. Replot of titration data showing 1 nM 18:0-fACP (▲), 0.7 nM 17:0-fACP (●), 1.3 nM 16:0-fACP (♦). Solid lines are the results of non-linear least squares fitting using equation 3 as described in Example 13.

DETAILED DESCRIPTION OF THE INVENTION

Figure 1A:
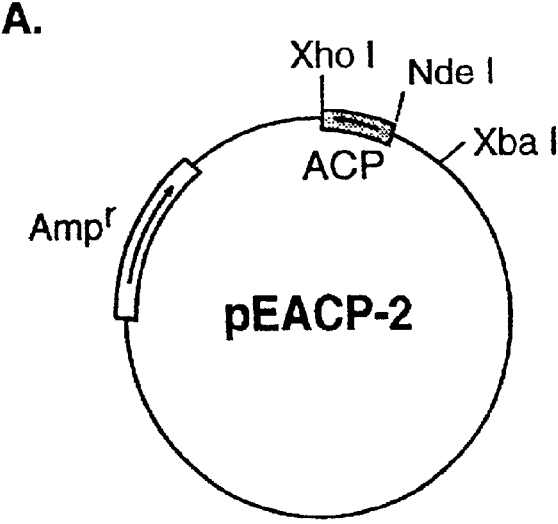
FIGS. 1A, 1B, and 1C. *Escherichia coli* ACP expression vectors.

Abbreviations:
"ACP"=acyl carrier protein.
"apo-ACP"=form of ACP lacking phosphopantetheine.
"nitroTyr-ACP"=form of ACP chemically modified at $C^\epsilon$ of Tyr71 to 3-nitroTyr-ACP.
"aminoTyr-ACP"=3-aminoTyr-ACP.
"dansylaminoTyr-ACP" or "dACP"=3-aminoTyr-ACP modified to contain a dansyl group on the amino group.
"fACP"=3-aminotyrosyl-ACP containing fluorescein covalently attached to the ε-amino group of chemically derivatized Tyr71 of E. coli ACP.
"n:0-ACP"=ACP with an n-carbon saturated fatty acid covalently attached to ACP through a phosphopantetheine thioester bond. Dansyl and fluorescein analogs designated "n:0-dACP" and "n:0-fACP,", respectively.

"n:1-ACP"=ACP with an n-carbon mono-unsaturated fatty acid covalently attached to ACP through a phosphopantetheine thioester bond. Dansyl and fluorescein analogs designated
"n:1-dACP" and "n:1-fACP,", respectively.
"holo-ACP"=biologically active form of ACP containing phosphopantetheine.
"ACPS"=holo-ACP synthase.
"AAS"=acyl-ACP synthetase.
"18:0-ACP"=stearoyl-ACP.
"18:1-ACP"=oleoyl-ACP.
"GC-MS"=tandem gas chromatography and mass spectrometry.
"ESI-MS"=electrospray ionization mass spectrometry.
"Δ9D"=18:0-ACP $\Delta^9$ desaturase.
"Fd"=*Anabaena* 7120 vegetative (2Fe-2S) ferredoxin.
"FdR"=*Zea mays* NADPH:ferredoxin oxidoreductase.
"non-radioactive-label"=any non-radioactive moiety that can be followed optically and/or spectroscopically in a chemical or enzymatic reaction. Explicitly includes fluorophores and chromophores.
"$OD_{600}$"=optical density at 600 nm.
"PCR"=polymerase chain reaction.
"T4moD"=11.6 kDa effector protein of the toluene-4-monooxygenase complex.
Acyl Carrier Protein (ACP):

As used herein, the term acyl carrier protein (ACP) denotes any acyl carrier protein, derived from any source whatsoever (naturally-derived, semi-synthetic, fully-synthetic) that includes at least one tyrosine residue. In many ACPs, a tyrosine residue is located in a position near to the C-terminal, as is the case with E. coli ACP. In other cases, a tyrosine residue is located near to the conserved serine residue that acts as the site of phosphopantetheinylation. In a limited number of cases, tyrosine residues are present in both locations. A tyrosine residue is found in the ACPs of every bacterial genus that has an entry in GenBank. Thus, it is very likely that other organisms not presently cataloged within GenBank will also have ACPs that include a suitable tyrosine residue. Organisms cataloged with GenBank that have an ACP having at least one tyrosine residue (and are thus ACPs that can be used in the present invention) include: *Bacillus, Clostridium, Haemophilus influenza, Klebsiella pneumoniae, Mycobacterium, Mycoplasma pneumonia, Neisseria meningitidis, Pseudomonas aeruginosa, Salmonella typhimurium, Shigella dysenteria, Streptococcus pyogenes, Treponema pallidum*, and *Vibrio cholerae*. Other organisms that are not cataloged within GenBank, but that are believed to have ACPs that contain at least one tyrosine residue include, without limitation: *Borellia burgdorferi, Bortedella, Brucella, Corynebacterium, Listeria monocytogenes, Staphylococcus*, and *Yersinia pestis*.

Thus, any ACP isolated from or derived from any of these sources and modified to contain a non-radioactive label as described herein, falls within the scope of the present invention.

Non-radioactive Labels:

At the heart of the present invention is the introduction of a non-radioactive label to an ACP. The present inventors have discovered that a label can be covalently bonded to a tyrosine residue of ACP, without effecting the reaction kinetics of the ACP. The nature of the label itself is not critical to the functionality of the invention, so long as the label can be made to react with the amino modification to the tyrosine residue of the ACP. The non-radioactive label can be a fluorophore, a chromophore, or any other chemical moiety that can be tracked optically or spectroscopically. It is preferred that the non-radioactive label be a fluorophore; dansyl and fluorescein are the particularly preferred fluorophores. Other preferred fluorophores include TRITC (tetramethylrhodamine isothiocyanate), FITC (fluorescein isothiocyanate), rhodamine, "Texas Red," and the like.

A host of suitable chromophores and fluorophores for use in the present invention are available commercially. A particularly abundant commercial source is Molecular Probes, Inc., of Eugene, Oreg. A non-limiting list of non-radioactive labels that can be used in the present invention includes the following (listed by Molecular Probes' catalog number; brief description, and Chemical Abstracts reference number for the fluorophore (where available):

| Molecular Probes' Catalog Number | Description (All trademarks property of Molecular Probes) | Chemical Abstracts Number (where available) |
|---|---|---|
| F2610 | FluoReporter ® Biotin-XX Protein Labeling Kit | 89889-52-1 |
| F6153 | FluoReporter ® Oregon Green ® 488 Protein Labeling Kit | 198139-51-4 |
| F-6155 | FluoReporter ® Oregon Green ® 514 Protein Labeling Kit | N/A |
| F-6161 | FluoReporter ® Rhodamine Red ™-X Protein Labeling Kit | N/A |
| F-6162 | FluoReporter ® Texas Red ®-X Protein Labeling Kit | 216972-99-5 |
| F-6163 | FluoReporter ® Tetramethylrhodamine Protein Labeling Kit | 246256-50-8 |
| F-6347 | FluoReporter ® Mini-biotin-XX Protein Labeling Kit | N/A |
| F-6348 | FluoReporter ® Biotin/DNP Protein Labeling Kit | N/A |
| F-6433 | FluoReporter ® Fluorescein-EX Protein Labeling Kit | N/A |
| F-6434 | FluoReporter ® FITC Protein Labeling Kit | 3326-32-7 |
| R-363 | resorufin, sodium salt | 635-78-9 |
| A-191 | 7-amino-4-methylcoumarin | 26093-31-2 |
| C-2110 | CellTracker ™ Blue CMAC (7-amino-4-chloromethylcoumarin) | N/A |
| C-12881 | CellTracker ™ Blue CMF$_2$HC (4-chloremethyl-6,8-difluoro-7-hydroxycoumarin) | N/A |
| C-183 | 3-cyano-7-hydroxycoumarin | 19088-73-4 |
| D-6566 | 6,8-difluoro-7-hydroxy-4-methylcoumarin (DiFMU) | 215868-23-8 |
| E-6578 | ELF ® 97 alcohol | N/A |
| F-1300 | fluorescein | 2321-07-5 |
| H-6482 | 7-hydroxy-9H-(1,3-dichloro-9,9-dimethylacridin-2-one) (DDAO) | 118290-05-4 |
| H-189 | 7-hydroxy-4-methylcoumarin | 90-33-5 |
| P12925 | 5-(pentafluorobenzoylamino)fluorescein (PFB-F) | N/A |
| R-6479 | rhodamine 110 (R110) | 13558-31-1 |
| T-659 | β-trifluoromethylumbelliferone (7-hydroxy-4-trifluoromethylcoumarin) | 575-03-1 |

Overview:

In this work, the efficient modification of Tyr71 in apo-ACP was described. The reported chemical modifications create a single, well defined location for placement of a fluorescent label. DansylaminoTyr-ACP was phosphopantetheinylated and acylated in high yield, and the steady-state kinetic competence of 18:0-dansylaminoTyr-ACP for desaturation by Δ9D was demonstrated. Taken together, these methods provide milligram quantities of purified ACP containing both acyl chains and fluorescent reporters.

To facilitate further studies of Δ9D substrate selectivity, a specific site of attachment of a fluorescent probe to ACP was desired. Since E. coli ACP contains at least one of every polar and charged amino acid, modification strategies directed toward these amino acids were unlikely to give the desired unique labeling. Furthermore, a role for N-terminal residues in ACP stability has previously been reported.[26] Thus labeling of the N-terminus was not desirable.

The o-nitration of tyrosine with tetranitromethane followed by reduction with sodium dithionite produces o-aminotyrosine, and this introduces a new amine group into the protein with a unique $pK_a$ value of ~4.75.[21,27] Because the sole Tyr residue (Tyr71) of E. coli ACP is near the C-terminus, and because modification of the C-terminus of spinach ACP did not alter reactivity with ACPS, AAS, or Δ9D,[11,15] Tyr71 was targeted for chemical modification and subsequent attachment of a dansyl group.

Figure 2A:
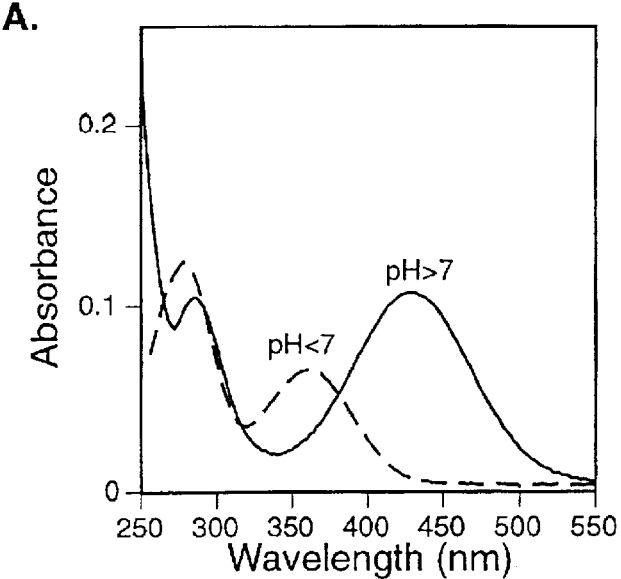
FIGS. 2A and 2B. Characterization of purified nitroTyr-ACP.
Figure 3A:
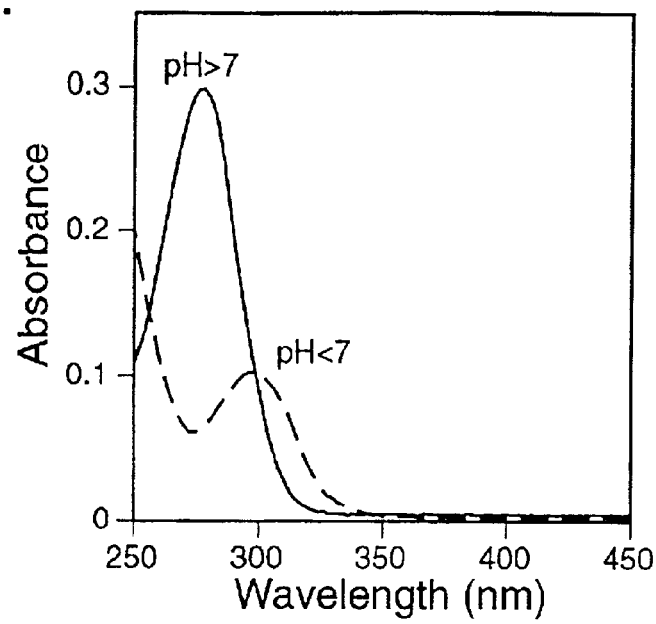
FIGS. 3A and 3B. Characterization of purified aminoTyr-ACP.

As previously reported,[28] the nitration of apoTyr71 -ACP required slightly higher temperature than for the same reaction with free tyrosine.[21] While this suggested that the ACP polypeptide may hinder reaction of Tyr71, purified nitroTyr-ACP had a pH-dependent optical spectrum (FIG. 2A) that was nearly identical to 3-nitrotyrosine.[21] NitroTyr-ACP was also readily reduced to aminoTyr-ACP under identical conditions to those reported for 3-nitrotyrosine,[27] fielding the corresponding change in absorbance spectrum (FIG. 3A).

Expression and In Vivo Modification of Recombinant ACP:

The vector pEACP-2 (FIG. 1A) has a T7 promoter and does not constitutively express lac$^Q$, resulting in uncontrolled basal expression. Consequently, liquid cultures inoculated with pEACP-2 transformants did not reach observable densities (Table 1). However, when acpP was cloned into a vector containing the T7lac promoter and the lac$^Q$ gene for constitutive expression of lac repressor (pBHF-5, FIG. 1B), cells were capable of growth and expression of ~105 mg/L ACP (Table 1). During these fermentations, the culture density reached a maximum ~2 h after induction with lactose at 37° C., and then the culture density began to decline rapidly. By decreasing the temperature to 30° C. at induction, the growth period could be extended to ~4 h, but this change did not increase the yield of purified ACP (data not shown). The majority of ACP expressed from pBHF-5 cells was in the apo-form (Table 1, >95%). ESI-MS also revealed that the purified apo-ACP contained a fraction (~15%) with mass corresponding to an additional 131 Da, which likely corresponded to incomplete removal of the N-terminal Met following translation.[15, 20]

Figure 1B:
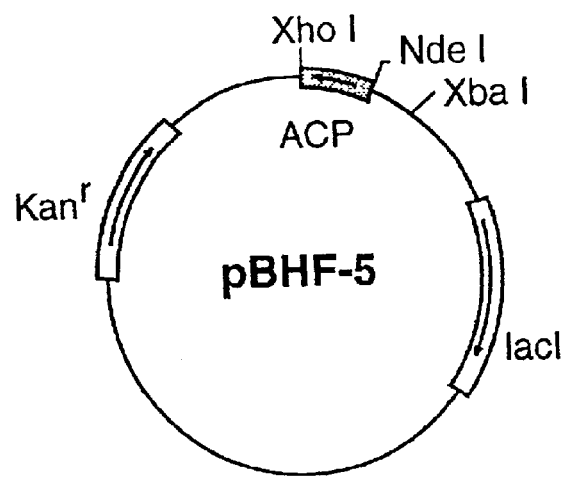
Figure 1C:
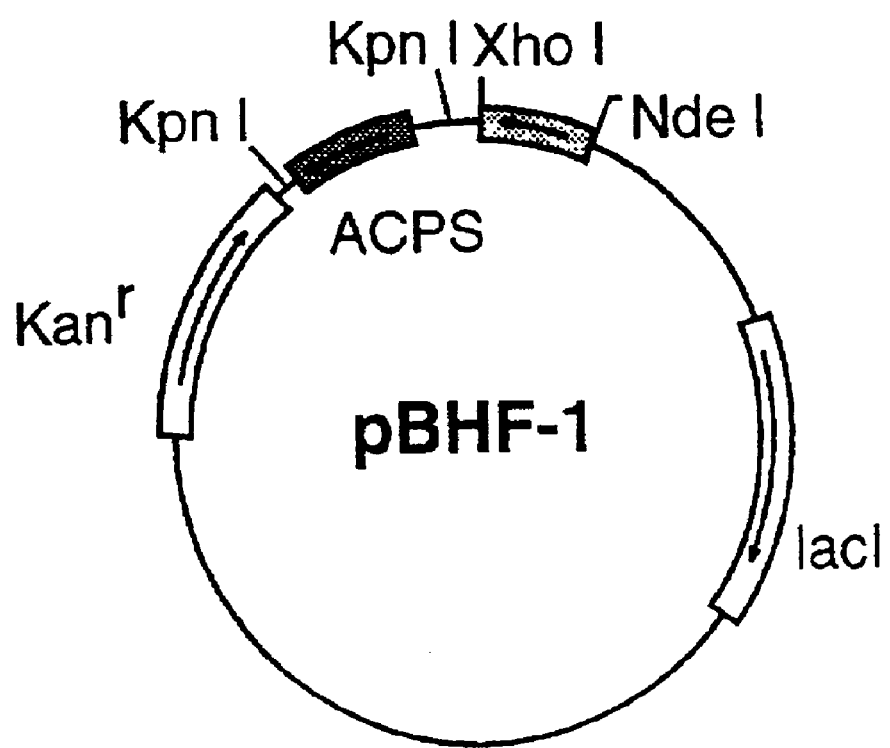

Coexpression of ACPs from either spinach or Streptomyces with E. coli ACPS gave predominantly holo-ACP. FIG. 1C shows a similarly constructed bicistronic vector containing both E. coli acpP and acpS under control of the T7lac promoter. While pBHF-1 transformants grown in minimal medium containing glucose as the carbon source did not express either ACP or ACPS, ~15 mg/L of ACP was obtained from coexpression in Luria Bertani medium, with ~50–75% of the recovered ACP in the holo-ACP form (Table 1).

When pBHF-1 transformants were grown in minimal medium containing fructose as the carbon source, approximately the same amount of ACP was recovered (14 mg/L, Table 1). However, in the fructose medium, essentially complete posttranslational phosphopantetheinylation was obtained (>95%, Table 1).

TABLE 1

Comparison of E. coli ACP Expression Plasmids and Medium Composition with Purification Yield and Percentage Phosphopantetheinylation.

| Plasmid Name | Plasmid Description | Growth Medium | Biomass[a] at harvest (g × L$^{-1}$) | ACP yield (Mg × L$^{-1}$) | % Holo-ACP observed[b] |
|---|---|---|---|---|---|
| pEACP-2[c] | pET-17, acpP | Luria Bertani | 0 | — | — |
| pBHF-5 | pET-28, acpP | Luria Bertani | 0.9 | 105 | <5 |
| pBHF-1 | pET-28, acpP, acpS, lacI$^Q$ | Minimal[d] Glucose | 1.4 | 0 | n.d.[e] |
| pBHF-1 | pET-28, acpP, acpS, lacI$^Q$ | Luria Bertani | 0.9 | 15 | 50–75 |
| pBHF-1 | pET-28, acpP, acpS, lacI$^Q$ | Minimal[d] Fructose | 1.6 | 14 | >95 |

[a]One gram of dry biomass corresponds to ~7.6 g of wet cell paste used in the purification procedures.
[b]Percentage of phosphopantetheinylated ACP observed in purified ACP preparations.
[c]Insufficient cell growth was obtained in 500 mL cultures to inoculate the fermenter.
[d]The minimal medium[16] was supplemented with 2 g/L Casamino acods.
[e]Not determined.

Figure 2B:
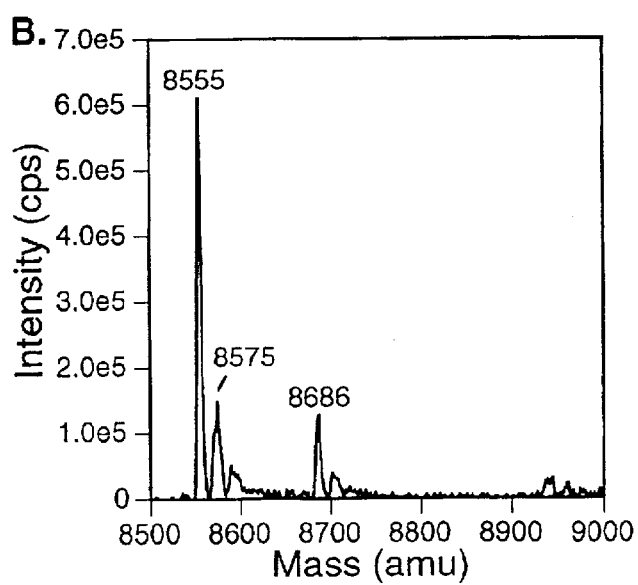

Nitration of Tyr71 of Apo-ACP:

Apo-ACP was used as a substrate for the nitration reaction in order to eliminate the requirement to protect chemically the unique, free thiol group found in holo-ACP. The nitration reaction gives substitution at the $C^e$ position of Tyr.[21] A mixture of mono- and dinitro-ACP species was obtained from this reaction. These species were resolved by native-PAGE and gel filtration chromatography, and were further characterized by ESI-MS (data not shown). NitroTyr-ACP was purified in ~80% yield (Table 3) by gel filtration chromatography. FIG. 2A and 2B show the absorbance spectrum and ESI-MS spectrum of purified nitroTyr-ACP, respectively. NitroTyr-ACP had a pH dependent absorption spectrum (FIG. 2A) that was nearly identical to authentic 3-nitrotyrosine and also displayed an isosbestic point at 381 nm.[21] The ESI mass spectrum (FIG. 2B, Table 2) contained two peaks corresponding to the calculated molecular weight of nitroTyr-ACP without N-terminal Met (8555 Da) and nitroTyr-ACP with N-terminal Met (8686 Da).

TABLE 2

Summary of Chemical Modifications of Apo-ACP as Determined by Electrospray Ionization Mass Spectrometry

| ACP Species[a] | Calculated mass (Da) | Observed mass[b] (Da) |
|---|---|---|
| apo-ACP | 8508 | 8508 |
| NitroTyr-ACP | 8553 | 8555 |
| AminoTyr-ACP | 8523 | 8524 |
| DansylaminoTyr-ACP | 8757 | 8757 |

[a]Mass observed for ACP following modification and purification.
[b]In addition to the appropriate chemical modification, a fraction of ACP (~15%) that contained the calculated mass for retention of the N-terminal Met was also observed.

Figure 3B:
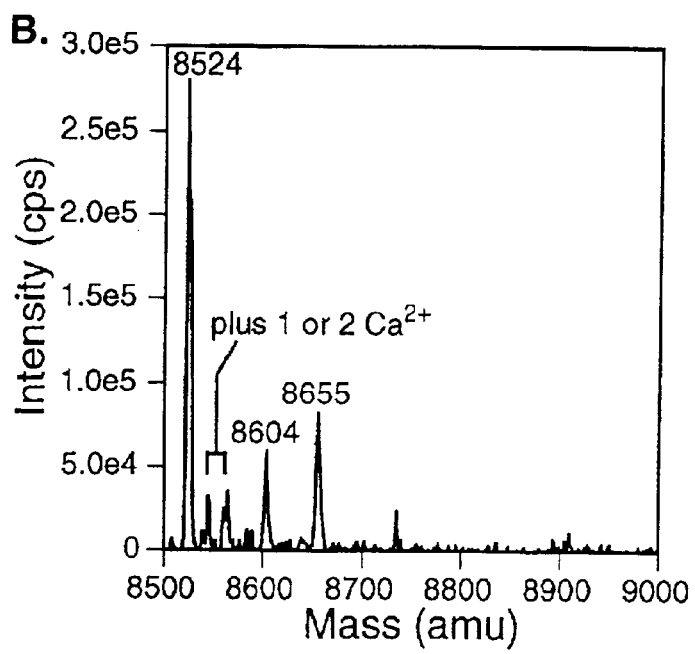

Reduction of NitroTyr-ACP to AminoTyr-ACP:

NitroTyr-ACP was reduced to aminoTyr-ACP by sodium dithionite. In anaerobic samples, the 430 nm absorbance of nitroTyr-ACP was lost within 2 min after the addition of sodium dithionite, and a new absorbance feature was observed at 275 nm (FIG. 3A). The optical band was also pH sensitive and the maximum shifted to ~300 nm at pH 5.5. ESI-MS of the reduction product verified the conversion of nitroTyr- to aminoTyr-ACP (FIG. 3B), and again revealed two major species corresponding to aminoTyr-ACP with and without K-terminal Met (8524 Da and 8655 Da, respectively) in the same percentage as the starting nitroTyr-ACP preparation.

Figure 4A:
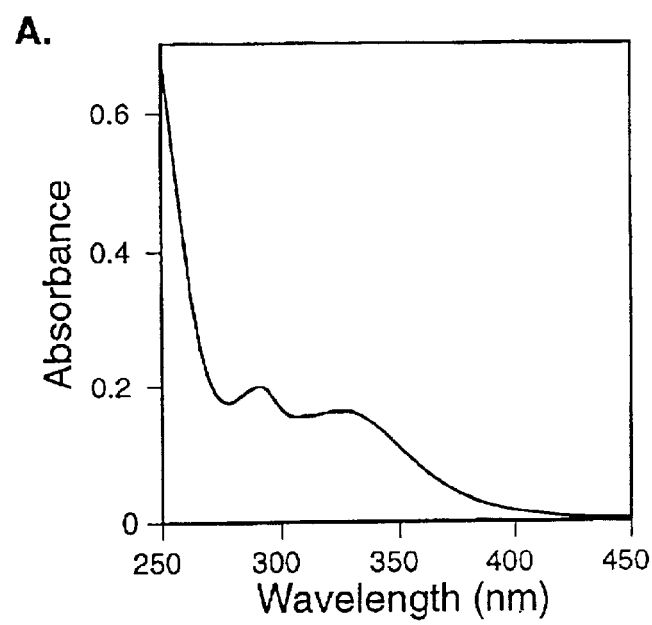
FIG. 4A: absorbance spectrum in 50 mM MNES, pH 5.5 (dashed-line) or 50 mM Tris pH 8.8 (solid-line).
Figure 4B:
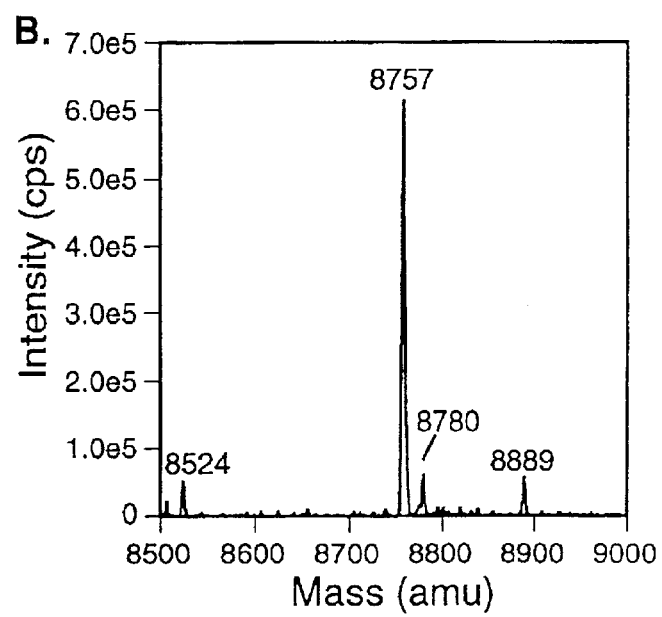
Figures 5A, 5B:
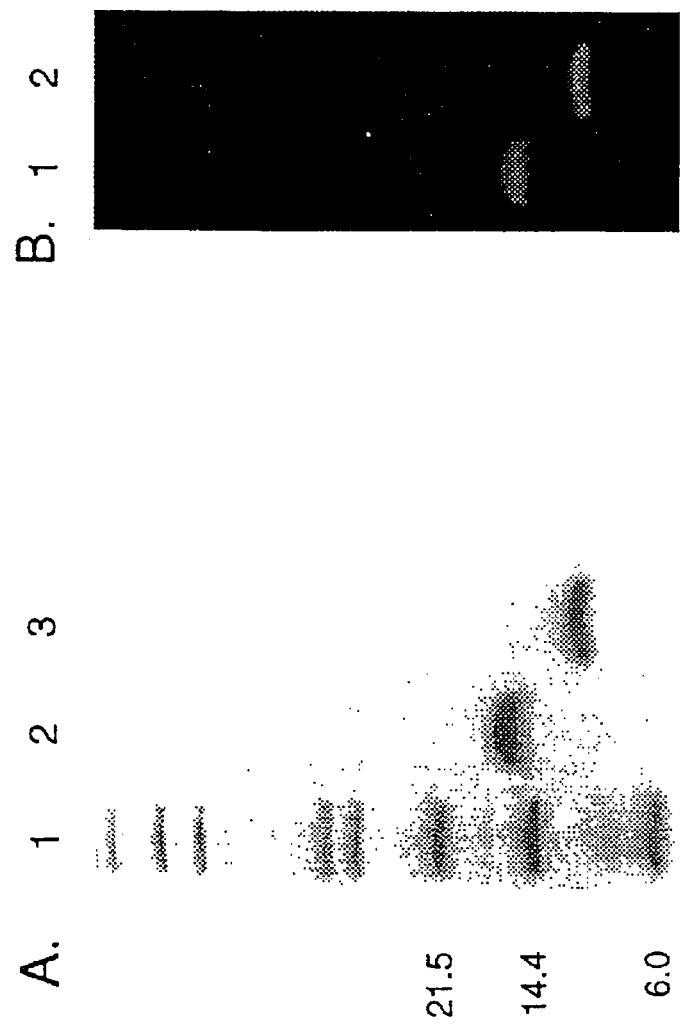
FIGS. 5A and 5B. Denaturing electrophoresis gel showing dansylaminoTyr-ACP and 18:0-dansylaminoTyr-ACP.

Dansylation of AminoTyr-ACP:

The dansylation of aminoTyr-ACP was performed at pH 5.0 in order to reduce the modification of other amine groups present in ACP. Under these conditions, apo-ACP was not dansylated in a control reaction after 1 h at room temperature as determined by native-PAGE and either UV illumination or Coomassie staining. The reaction of aminoTyr-ACP with dansyl chloride typically produced a mixture of mono- and didansylated ACP products (~65% and ~35% respectively, as determined by native-PAGE). DansylaminoTyr-ACP was purified from didansyl-ACP by anion exchange chromatography in succinate buffer at pH 5.0. The optical and ESI-MS spectra of purified dansylaminoTyr-ACP are shown in FIGS. 4A and 4B, respectively. The absorbance spectrum (FIG. 4A) was similar to that reported for dansyl-aminotyrosine model compounds,[22] and exhibited absorption maxima at 290 and 325 nm. DansylaminoTyr-ACP was also detected in native-PAGE gels by UV irradiation (FIGS. 5A and 5B). ESI-MS revealed one predominant peak (~90%, FIG. 4B), corresponding to the predicted mass of dansylaminoTyr-ACP minus the N-terminal Met (8757 Da). The sample also contained small fractions of dansylaminoTyr-ACP plus the N-terminal Met (8889 Da) and aminoTyr-ACP (8524 Da).

Phosphopantetheinylation and Acylation of DansylaminoTyr-ACP:

The in vitro phosphopantetheinylation of dansylaminoTyr-ACP was performed as previously reported for spinach ACP.[15] Subsequent reaction with AAS and stearic acid yielded 18:0-dansylaminoTyr-ACP in greater than 95% yield as determined by denaturing gel electrophoresis (FIG. 5A lane 3 and FIG. 5B, lane 2) and by DTNB assay (data not shown). FIG. 5B (lanes 1 and 2, respectively) shows the fluorescence emission from dansylaminoTyr-ACP and 18:0-dansylaminoTyr-ACP when the denaturing electrophoresis gel was illuminated with reflected UV light. The overall yield for production of 18:0-dansylaminoTyr-ACP starting from 55 mg of unmodified apo-ACP was 17 mg (31%, Table 3).

TABLE 3

Recovery of Chemically Modified Apo-ACP During the Synthesis of DansylaminoTyr-ACP

| Step[a,b] | Volume (mL) | Total Protein (mg) | Yield (%) |
|---|---|---|---|
| apo-ACP | 5 | 55 | 100 |
| Nitration | 35 | 45 | 83 |
| Reduction | 70 | 35 | 64 |
| Dansylation | 20 | 17 | 31 |
| Acylation[c] | 2.3 | 17 | 31 |

[a]Apo-ACP was quantitated by Bradford assay[29].
[b]Modified apo-ACPs were quantitated by optical spectroscopy using the following molar absorptivities: nitroTyr-ACP, $\epsilon_{381}$ = 2200 $M^{-1}$ $cm^{-1}$; aminoTyr-ACP, $\epsilon_{302}$ = 4200 $M^{-1}$ $cm^{-1}$; DansylaminoTyr-ACP, $\epsilon_{320-360}$ 4200 $M^{-1}$ $cm^{-1}$.
[c]18:0-dansylaminoTyr-ACP was quantitated as described in the Examples.

Purification of Acyl-ACP by Preparative Native-PAGE:

The in vitro acylation of ACP using AAS and 10:0 to 18:0 fatty acids produced high yields of acyl-ACP.[23] In contrast, reactions performed with unusual fatty acids gave moderate yields (~40–60%, J. Haas, J. Broadwater, B. Laundre, B. Fox unpublished results). Therefore, preparative scale native-PAGE was investigated as a method to purify acyl-ACPs from holo- and apo-ACP on a 100 mg (~12 μmol) scale. The high pH (9.0) of the buffer system yielded an $R_f$ value of 1 for E. coli acyl-ACP, and consequently, minimized the time required for electrophoresis. However, the alkaline pH contributed to the relative lability of the thioester linkage of acyl-ACP. At pH 9, recovery of acyl-ACP from 5 cm gels was 45%, while the use of a 3.5 cm gel reduced the electrophoresis time and improved the recovery of acyl-ACP to 77%. Further trials revealed that the 3.5 cm gel was the minimum length that could still provide complete resolution of acyl-ACP from holo-ACP at the desired loading. The use of a pH 7.4 buffer system, which should have given improved stability of the thioester bond, resulted in a complete loss of acyl-ACP due to a dramatic decrease in R- and corresponding increase in electrophoresis time.

Figure 6A:
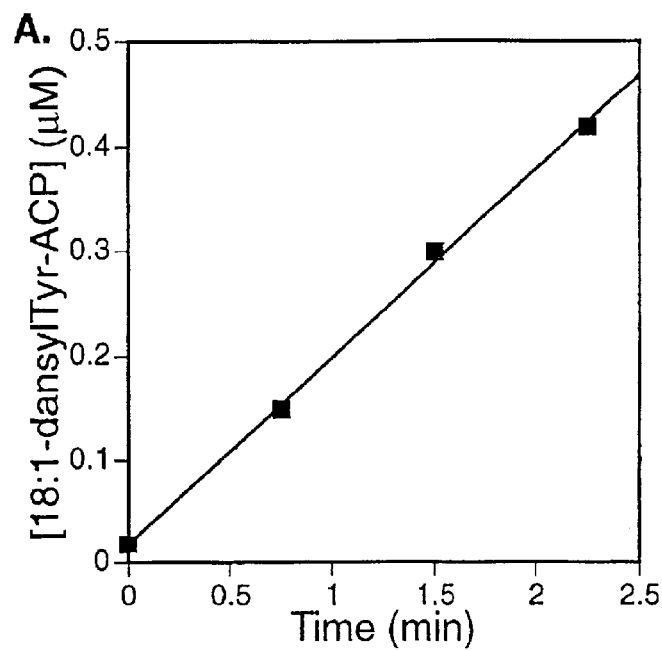
FIGS. 6A and 6B. Desaturation of 18:0-dansylaminoTyr-ACP.
Figure 6B:
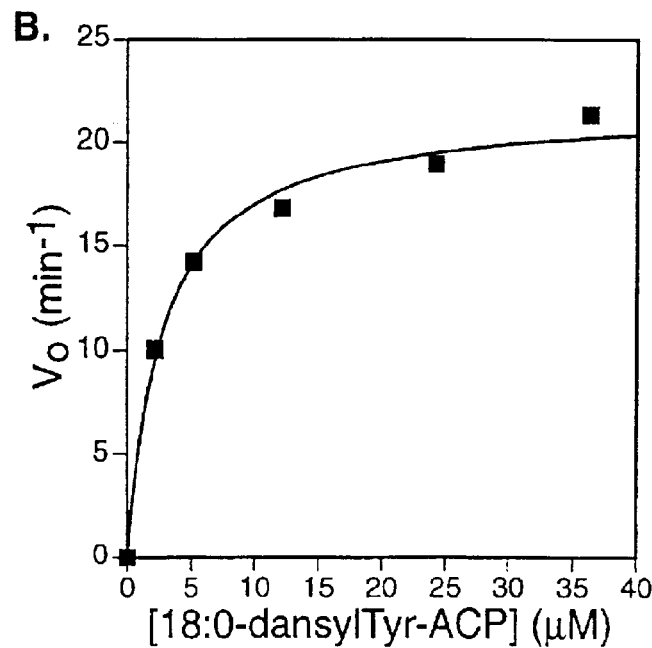

Desaturation of 18:0-dansylaminoTyr-ACP:

A steady-state kinetic analysis of $k_{cat}/K_M$ was recently reported for the reaction of Δ9D with 15:0- to 19:0-ACPs.[11] This study revealed the importance of acyl chain length on catalytic enhancement. To evaluate the effect of the dansyl modification on catalysis by Δ9D, the steady-state kinetic parameters $k_{cat}$=22±0.76 $min^{-1}$ and $K_M$=2.7±0.43 μM were determined for the Δ9D-catalyzed desaturation of 18:0-dansylaminoTyr-ACP (FIGS. 6A and 6B). These values are similar to those previously determined for 18:0-ACP ($k_{cat}$= 33±0.80 $min^{-1}$, $K_M$=3.3±0.42 μM).[11] Furthermore, the selectivity for 18:0-dansylaminoTyr-ACP ($k_{cat}/K_M$=8 $μM^{-1}$•$min^{-1}$) was closer to that observed for 18:0-ACP ($k_{cat}/K_M$= 10 $μM^{-1}$•$min^{-1}$) than for 17:0-ACP ($k_{cat}/K_M$=2.5 $μM^{-1}$ $min^{-1}$).[11] In addition, no change in the positional specificity for double bond insertion was observed for 18:0-dansylaminoTyr-ACP. These measurements demonstrate the competency of 18:0-dansylaminoTyr-ACP as a substrate for Δ9D.

Apparent Toxicity of apo-ACP:

The apparent toxicity of acpP overexpression to E. coli has been previously reported.[24] This conclusion is supported by the lack of cell growth observed from transformants containing the poorly regulated pEACP-2 (see Table 1) and the behavior of tightly regulated pBHF-5 transformants after induction. The use of pET28(a), which contains the T7lac promoter and $lac^Q$ (pBHF-5, FIG. 1B), gave a similar level of ACP expression (Table 1) to that obtained previously with the pET-pLysS system.[20] However, the pET28-based construct does not produce lysozyme, which can lead to autocatalytic culture lysis in vigorously stirred fermenters. The yield of purified ACP obtained from coexpression with ACPS (in either Luria Bertani or minimal medium) was lower than that obtained when ACP was expressed without ACPS (Table 1). However, since the pBHF-1 coexpression vector also yielded large quantities of ACPS (~1:1 production based on examination of cell-free extracts in denaturing electrophoresis gels), this additional protein expression may have reduced the capacity for ACP production by the host cell.

Effect of Growth Medium on Posttranslational Modification of ACP:

Recently, Aristidou, et al. reported improved recombinant gene expression in E. coli when fructose was substituted for glucose as the carbon source.[25] This favorable result was postulated to arise from the tighter regulation of fructose transport into cells, which resulted in a lowering of the Crabtree effect and consequent acidogenesis.[25] As shown in Table 1 for pBHF-1 transformants, growth in a minimal medium containing glucose did not support the expression of either ACP or ACPS. However, when fructose was substituted for glucose, the same pBHF-1 transformants were capable of expression and efficient posttranslational modification of ACP (~14 mg/L, >95% holo-ACP). While the molecular basis for the increased posttranslational modification remains unknown, it nevertheless suggests an expanded potential for the use of fructose as a carbon source for recombinant E. coli fermentations.

Characterization of Dansylaminotyrosyl-ACP:

Dansylation of aminoTyr-ACP yielded dansylaminoTyr-ACP (~65%) and a didansylated product (~35%). Since a control reaction with apo-ACP did not yield dansylated protein, the presence of either 3-aminoTyr or dansylamino-Tyr may enhance the reactivity of a remote site on ACP. DansylaminoTyr-ACP was purified from the didansyl species by anion exchange chromatography and the absorbance spectrum of dansylaminoTyr-ACP (FIG. 4A) was similar to that of dansylaminoTyr model compounds.[22] DansylaminoTyr-ACP behaved indistinguishably from apo-ACP during in vitro phosphopantetheinylation and acylation (FIGS. 5A and 5B), thus showing that the dansylated version reacts in the same fashion as the unmodified susbstrate.

Furthermore, the presence of dansylaminoTyr had no significant effect on the desaturation reaction (FIG. 6B), and the $k_{cat}/K_M$ of approximately 8 $μM^{-1}$ $min^{-1}$ determined for 18:0-dansylaminoTyr-ACP was similar to that of 18:0-ACP ($k_{cat}/K_M$=10 $μM^{-1}$ $min^{-1}$).[11] Taken together, these results show that dansylation of Tyr71 does not alter the reactivities of three different enzymes that utilize various forms of ACP as a substrate. This labeled ACP substrate is thus highly useful as a catalytically-silent spectroscopic probe of protein-protein interactions during the desaturase reaction (and other reactions involving ACPs).

EXAMPLES

The following Examples are included solely to provide a more thorough and consistent understanding of the invention disclosed and claimed herein. The Examples do not limit the scope of the invention in any fashion.

Chemicals, Enzymes, Plasmids, and Bacterial Strains:

Restriction endonucleases, T4 DNA ligase, calf intestinal phosphatase, and "Deep Vent"-brand DNA polymerase were purchased from New England BioLabs (Beverly, Mass.). Coenzyme A and pantothenic acid hemicalcium salt were obtained from Sigma (St. Louis, Mo.). Nucleotide triphosphates were purchased from Pharmacia Biotech (Piscataway, N.J.). Oligonucleotide primers were synthesized by Integrated DNA Technologies, Inc. (Coralville, Iowa). AAS, ACPS, Δ9D, FdR, and Fd were expressed, purified, and characterized as previously described.[15] Tetranitromethane and stearic acid were purchased from Aldrich (Milwaukee, Wis.). Dansyl chloride was purchased from Molecular Probes (Eugene, Oreg.). The E. coli strain DH5a {supE44 lacU169(f80 lacZ M15)hsdR17recA1 endA1 gyrA196 thi-1 reLA1} (available commercially from Invitrogen, Carlsbad, Calif.) was used for general cloning steps. The E. coli strain BL21(DE3) {F- ompThsdS$_B$ ®B-mB-) gal dcm (DE3)} (also available from Invitrogen) was used as the expression host.

Example 1

Plasmid Construction

The isolation of plasmid DNA and all other cloning manipulations were carried out according to established procedures.[16] Purified E. coli K12 genomic DNA was used as template for PCR amplification of the E. coli acpP gene.

The forward primer incorporated an NdeI restriction site (capitalized) at the start codon:

5'-ccgcaCATATGagcaccatcgaagaacgtgtg-3' (SEQ. ID. NO: 1).

The reverse primer incorporated a XhoI site (capitalized) after the stop codon:

5'-caataCTCGAGttacgcctggtggccgttgatg -3' (SEQ. ID. NO: 2).

The resulting ~300 bp amplified fragment was purified by gel electrophoresis and extracted using the "QIAEX II"-brand extraction kit (Qiagen, Valencia, Calif.). The purified PCR product was blunt-end ligated into the EcoRV site of pZero-2 (Invitrogen) using T4 DNA ligase. The ligation reaction was used to transform CaCl$_2$ competent E. coli DH5a by heat shock. The transformation mixture was plated onto Luria-Bertani agar plates containing 50 μg/mL kanamycin. Plasmids were isolated from kanamycin-resistant transformants using the "Mini-Prep"-brand isolation kit (Promega, Madison, Wis.) and screened for the correct insert by restriction mapping. The sequence of the amplified acpP gene was verified by cycle sequencing using "AmphTaq"-brand DNA polymerase, FS (Perkin-Elmer, Culver City, Calif.) and dye-labeled terminators at the University of Wisconsin Biotechnology Center. The acpP gene was removed from the pZero-2 vector by double digestion with NdeI and XhoI and ligated into similarly digested and gel-purified pET17(b) (Novagen, Madison, Wis.). The ligation mixture was used to transform competent E. coli DH5a and plated onto Luria-Bertani agar plates containing 100 μg/mL ampicillin. Plasmids were isolated and characterized as described above, and a correctly constructed plasmid was named pEACP-2 (FIG. 1A). The acpP gene was also subcloned from pEACP-2 by double digestion with XbaI and XhoI and ligated into similarly digested pET28(a) (encoding kanamycin resistance). This new vector was called pB HF-5 (FIG. 1B).

A coexpression vector containing the E. coli acpP and acpS genes was constructed as previously described for the coexpression vector containing the spinach acpP and E. coli acps genes.[15] This vector was named pBHF-1 (FIG. 1C).

Example 2

Media and Fermentation Protocols

Fermentations were done in a 10-L New Brunswick Scientific BIOFLO 3000 bench-top fermenter (New Brunswick, N.J.). The pH was maintained at 7.1 by the controlled addition of 4 M NH$_4$OH and 4 M H$_2$SO$_4$. The dissolved O$_2$ level was maintained at 30% of air saturation or greater by variation of the agitation rate. Foaming was suppressed by manual addition of antifoam (Mazu DF 204, PPG Industries, Gurnee, Ill.). Kanamycin was not added to the culture-medium in the fermenter. The cells were harvested by centrifugation at 4400g for 15 min in a Beckman J-6B centrifuge equipped with a JS-5.2 rotor (Beckman, Fullerton, Calif.).

For batch fermentations in Luria Bertani medium, E. coli BL21 (DE3) was transformed with pBHF-1 or pBHF-5 and plated onto Luria Bertani agar plates containing 50 μg/mL kanamycin. After 16 h, a single colony was aseptically transferred into a sterile test tube containing 5 mL of Luria Bertani medium and 50 μg/mL kanamycin. The culture was grown with shaking at 37° C. until the OD$_{600}$ reached ~0.8; 50 μL of this culture was then used to inoculate each of two 2-L flasks containing 500 mL of Luria Bertani medium and 50 μg/mL kanamycin. The two 500 mL cultures were grown at 37° C. until the OD600 reached ~1; 1 liter was then used to inoculate the fermenter containing 9 liters of Luria Bertani medium. The fermenter culture was grown at 37° C. until the OD$_{600}$ reached ~3. At this point, the culture was induced by the batch addition of filter-sterilized solutions of b-D-lactose (0.8% w/v), Casamino acids (0.2% w/v, Difco, Detroit, Mich.), and 0.05 g/L pantothenic acid hemicalcium salt. The induced culture was grown for 4 h, and yielded ~7 g/L of wet cell paste.

For batch fermentations in minimal medium supplemented with Casamino acids (0.2 g/L)[16] and using fructose as the carbon source, E. coli BL21(DE3) was transformed with pBHF-1 and starting inocula were prepared as described above except that the 2-L flasks contained 500 mL of minimal medium with 4 g/L of D-fructose, 2 g/L Casamino acids, and 50 μg/mL kanamycin. When the 500 mL cultures reached an OD$_{600}$ of ~1, they were used to inoculate a fermenter containing 9 liters of the same medium prepared without kanamycin. The culture grew to OD$_{600}$ ~7 before all of the fructose was consumed as indicated by a sudden increase in the dissolved O$^2$ concentration and corresponding drop in the agitation rate.[17] At this point, the cells were induced by the addition of lactose as described above, and the temperature was adjusted to 30° C. The induced culture was grown for 4–5 h, and yielded ~12 g/L of wet cell paste.

For batch fermentations in minimal medium supplemented with Casamino acids (0.2 g/L) and containing 6 g/L glucose, the procedures described above for fructose growth were used. The 6 g/L of glucose was depleted when the culture reached an OD$_{600}$~5–6, and induction, protein expression, and cell harvest were as described above. A yield of ~11 g/L of wet cell paste was obtained.

Example 3

ACP Purification

All purification steps were performed at 4° C. A 50 g block of frozen cell paste was broken into pieces and resuspended in 100 mL of 100 mM Tris, pH 8.0 in a stainless steel beaker.

Lysozyme, DNase, and RNase (0.15 mg of each, Sigma) were added to the suspension. The cell mixture was sonicated for a total of 6 min using 30 s pulses (Fisher Model 550 Sonic Dismembrator, ¾ inch disruptor horn, 100% of maximum output). During sonication, the temperature of the cell suspension was maintained below 7° C. by placing the beaker in an ice bath containing a saturated NaCl solution. The sonicated cell suspension was centrifuged at 39,000 g for 1 h to remove cell debris. The supernatant was diluted 2-fold with 25 mM MES, pH 6.1 and loaded onto a Fast Flow DEAE-Sepharose CL-6B (Pharmacia LKB Biotechnology Inc., Piscataway, N.J.) column (48×250 mm) equilibrated in 25 mM MES, pH 6.1. The column was washed with 0.75 L of 25 mM MES, pH 6.1. The protein was eluted in a 1.6 L linear gradient from 0 to 0.85 M NaCl in 25 mM MES, pH 6.1, at a linear flow rate of 3 cm/h. Fractions were analyzed by SDS-PAGE and peak fractions were pooled and concentrated by ultrafiltration (YM3 membrane, AMICON, Inc., Beverly, Mass.). The concentrated peak fractions were loaded onto a Sephacryl S-100 column (48×1000 mm) equilibrated with 25 mM MES, pH 6.1, containing 0.1 M NaCl and eluted at 6.6 cm/h. Peak fractions were analyzed by SDS-PAGE, pooled and concentrated by ultrafiltration.

Example 4

Nitration of Tyr71 of apo-ACP with Tetranitromethane

The nitration reaction mixture typically contained 240 µM apo-ACP (50 mg) in 50 mM Tris, pH 8.1. Tetranitromethane was added from a 0.84 M solution prepared in 95% ethanol to give a final concentration in the reaction mixture of 50 mM. The reaction mixture was stirred for ~2.5 h at 30° C. and stopped by precipitation of ACP with dilute acetic acid. NitroTyr-ACP was purified by gel filtration chromatography on a 26/10 HiPrep Sephacryl S-100 column (Pharmacia LKB Biotechnology Inc.) in 25 mM MES, pH 6.1, at a linear flow rate of 11 cm/h. Fractions containing pure nitroTyr-ACP were pooled based on examination of native-PAGE gels.

Example 5

Reduction of NitroTyr-apo-ACP to AminoTyr-apo-ACP

Pooled nitroTyr-ACP fractions were adjusted to pH 8.0 by the addition of 0.32 M Tris, pH 8.0 to give a final concentration of 50 mM Tris. The sample was then made anaerobic by repeated evacuation and flush with $O_2$-free Ar. The anaerobic sample of nitroTyr-ACP was reduced to aminoTyr-ACP by the addition of ~800 µL of 25 mg/mL sodium dithionite prepared in $O_2$-free 1 M potassium phosphate buffer, pH 7.0. The aminoTyr-ACP was exchanged into 50 mM sodium acetate buffer, pH 4.75, by repeated concentration and dilution using ultrafiltration.

Example 6

Dansylation of AminoTyr-apo-ACP

The dansylation reaction mixture contained 40 µM aminoTyr-ACP (~35–40 mg) in 50 mM sodium acetate, pH 5.0, containing 35% (v/v) acetonitrile. Dansyl chloride was prepared as a 15 mM dansyl chloride solution in acetonitrile. This solution was slowly added to the rapidly stirred reaction mixture to give a final concentration of 1.5 mM dansyl chloride. The reaction mixture was stirred at room temperature in the dark for 1 h, diluted 10-fold with 25 mM MES, pH 6.1, and loaded onto a 15 mL Fast Flow DEAE-Sepharose CL-6B column. The column was washed with 150 mL of 25 mM MES, pH 6.1, to remove acetonitrile and the dansyl-ACP was batch-eluted in the same buffer containing 0.75 M NaCl. This step also separated ACP from unreacted dansyl chloride, which formed a visible yellow precipitate on the column. The dansyl chloride was later removed by washing the column with 25 mM MES, pH 6.1, containing 80% (v/v) 2-propanol. The dansyl-ACP was precipitated by addition of dilute acetic acid to give a pH of ~3.9, and recovered by centrifugation. The resulting pellet was resuspended in 20 mL of 0.3 M MES, pH 6.1. DansylaminoTyr-ACP was purified from a didansyl-ACP species using a 16/10 HiLoad Q Sepharose Fast Flow column (Pharmacia LKB Biotechnology Inc.). The column was loaded with dansyl-ACP at a linear flow rate of 15 cm/h in 25 mM succinic acid, pH 5.0, washed with 100 mL of the 25 mM succinic acid, pH 5.0, and then washed with 100 mL of 25 mM succinic acid, pH 5.0, containing 0.05 M NaCl. The protein was eluted at a linear flow rate of 15 cm/h in a 300 mL linear gradient from 0.05 to 0.25 M NaCl in 25 mM succinic acid, pH 5.0. Fractions containing dansylaminoTyr-ACP or didansyl-ACP were identified by native-PAGE. Both dansylaminoTyr-ACP and didansyl-ACP could be detected by fluorescence on a light box under reflected 300 nm light (prior to Coomassie staining) or by Coomassie staining.

Example 7

In Vitro Phosphopantetheinylation and Acylation of Dansyl-ACP

Phosphopantetheinylation reactions typically contained ~40 µM dansylaminoTyr-ACP (~20 mg), 100 µM coenzyme A, 10 mM $MgCl_2$, and 1 µM ACPS in 50 mM Tris, pH 8.8. The reaction was incubated with stirring at 25° C. for 1 h, and terminated by addition of the acylation buffer to bring the final solution to 15 µM ACP, 0.4 M LiCl, 10 mM $MgCl_2$; ~2–3% Triton X-100, 5 mM ATP, 3 mM DTT, and 260 µM stearic acid (delivered as 70 µmol stearic acid dissolved in 1 mL toluene) in 50 mM Tris, pH 8.0. AAS (2.5 mg) was added and the reaction was stirred for ~16 h at 25° C. To purify acyl-ACP from the other reaction components, the acylation reaction was diluted 10-fold with 25 mM MES, pH 6.1, and loaded onto a 15 mL Fast Flow DEAE Sepharose CL-6B column. The column was successively washed with 150 mL of 25 mM MES, pH 6.1, 100 mL of an 80:20 (v/v) mixture of 2-propanol and 25 mM MES, pH 6.1, and 150 mL of 25 mM MES, pH 6.1. The purified acyl-ACP was eluted in 40 mL of 25 mM MES, pH 6.1, containing 0.75 M NaCl, and the eluate was adjusted to a pH of ~3.9 with dilute acetic acid to precipitate the acyl-ACP. The precipitated acyl-ACP was collected by centrifugation and resuspended in 0.1 M MES, pH 6.5.

Example 8

Electrophoresis Methods

Protein expression was detected by denaturing gel electrophoresis (70×80×0.75 mm gels, Bio-Rad, Hercules, Calif.) using 10% Tris-Tricine polyacrylamide gels and Coomassie Blue staining.[18] Protein standards were obtained from Novex (San Diego, Calif.). Chemical modification of apo-ACP Y71 was detected by native gel electrophoresis (70×80×0.75 mm gels). Continuous gels consisting of 13% acrylamide, 0.5% N,N'-methylenebisacrylamide, 43 mM imidazole, 35 mM HEPES, pH 7.4, and 1 M urea were used for detection of nitroTyr-ACP. A buffer containing 43 mM imidazole and 35 mM HEPES, pH 7.4 was used for both anode and cathode buffers. For detection of dansylaminoTyr-ACP, the same buffer system described for detection of nitroTyr-ACP was used with 16% acrylamide and 0.7% N,N'-methylenebisacrylamide gels.

Example 9

Purification of Acyl-ACP by Preparative Native-PAGE

For preparative native gel electrophoresis, a gel solution containing 13% acrylamide, 0.5% N,N'-methylenebisacrylamide, 0.37 M Tris, pH 9.0, and 1 M urea was degassed immediately prior to casting the gel in the Model 491 "PrepCell"-brand gel electrophoresis apparatus (BioRad, Hercules, Calif.). A 190 mM glycine, 25 mM Tris, electrophoresis/elution buffer was degassed by vacuum filtration immediately prior to electrophoresis. The pH of this buffer was not adjusted. The fractions from the eluate were analyzed with electrophoresis 70×80×0.75 mm slab gels using the same gel system as used in the "PrepCell"-brand apparatus.

Preparative-scale native-PAGE was carried out using a "PrepCell"-brand apparatus (Bio-Rad). A 37 mm diameter gel assembly tube was used to cast 3.5 or 5 cm length gels at 4° C. A typical sample contained 8–10 $\mu$mol of acyl-ACP in $\mu$3 mL of 0.1 M MES, pH 6.5, and was mixed with 1 mL of sample loading buffer (0.1 M Tris, pH 6.8, 30% (w/v) glycerol, and 0.03% (w/v) bromphenol blue) immediately prior to electrophoresis. The apparatus was used following the manufacturer's instructions at 7 W constant power. Peak fractions were pooled based on assay by UV detection and by examination of analytical native-PAGE gels. Pooled peak fractions were concentrated by precipitation with dilute acetic acid and the resuspended protein was separated from bromphenol blue using a G-25/150 gel filtration column (25×75 mm) equilibrated in 25 mM MES, pH 6.5. The purified acyl-ACP was concentrated by precipitation with dilute acetic acid and quantitated as described below.

Example 10

Quantitation of Acyl-ACPs

Acyl-ACPs were quantitated by hydrolysis of the thioester linkage followed by colorimetric determination of the free thiol present in holo-ACP using 5,5'-dithio-bis-(2-nitrobenzoic) acid (DTNB). The reaction mixture consisted of ~15–50 $\mu$M acyl-ACP in 200 $\mu$L of 60 mM NaOH (from a certified 0.25 N NaOH stock solution; Fisher, Springfield, N.J.) and was incubated at 40° C. for 10 min. The cleavage reaction was stopped and the reaction mixture was adjusted to neutral pH by addition of 50 $\mu$L of 0.25 M HCl (certified 0.25 N HCl stock solution; LabChem, Inc., Springfield, N.J.). The DTNB assay was performed by addition of 230 $\mu$L of terminated acyl-ACP cleavage reaction to 700 $\mu$L of 0.2 mM DTNB in 50 mM phosphate buffer, pH 7.0 in a quartz cuvette. The amount of thionitrobenzoate formed by reaction of holo-ACP with DTNB was determined using optical spectroscopy and a molar absorptivity of 13,600/(M) (cm) at 412 nm.[19] A control reaction where deionized water was substituted for both NaOH and HCl was used to estimate the background amount of holo-ACP.

EXAMPLE 11

Electrospray Ionization Mass Spectrometry

Protein mass spectra were obtained on a Perkin-Elmer-Sciex API 365 triple quadrupole electrospray ionization mass spectrometer at the Mass Spectrometry Facility of the University of Wisconsin Biotechnology Center. Samples were equilibrated with 20 mM ammonium acetate, pH 6.1, using a HiPrep 26/60 Sephacryl S-100 column (Pharmacia) at a flow rate of 11 cm/h to remove sodium. Alternatively, a Slide-A-Lyzer dialysis cassette (Pierce, Rockford, Ill.) was used to dialyze a 300 $\mu$L sample against three 1-liter changes of ammonium acetate buffer.

Example 12

Stearoyl-ACP $\Delta^9$ Desaturase Assay

In a typical assay, 1–50 nmol of 18:0-dansylaminoTyr-ACP, 0.2 nmol of FdR, 1 nmol of Fd, 0.02 nmol of $\Delta$9D, and 1700 nmol of NADPH were placed in 1 mL of 50 mM HEPES, pH 7.8, containing 50 mM NaCl in an open 5 mL autosampler vial. Reaction vials were shaken at 100 rpm in a 25° C. water bath. The reactions were started by the addition of $\Delta$9D and at timed intervals 200 $\mu$L aliquots were withdrawn and quenched by addition to 150 $\mu$L of tetrahydrofuran. Steady-state kinetic analysis was performed as previously described.[11] The fatty acyl-chains were reductively cleaved from ACP, extracted, derivatized, and quantitated by GC-MS as previously described.[11] The $k_{cat}$-values are reported with respect to diiron center concentration.[11]

Example 13

Binding Affinity Studies Using Dansyl-ACP (dACP) and Fluorescein-ACP (fACP)

Stearoyl-acyl carrier protein $\Delta^9$ desaturase ($\Delta$9D) catalyzes the NADPH and $O_2$ dependent regio- and stereo-specific insertion of a cis double bond at the C9 position of stearoyl-acyl carrier protein (ACP) to produce oleoyl-ACP. In this Example, steady-state and stopped-flow fluorescence anisotropy measurements using dansyl- and fluoresceinyl-acyl-ACPs revealed equilibrium dissociation constants and dissociation rate constants for 16:0-, 17:0-, and 18:0-ACPs with resting and chemically 4e$^-$ reduced $\Delta$9D. Binding of 18:0-fACP to one subunit of the dimeric resting $\Delta$9D was observed with $K_{D1}$=13 nM. No significant difference in the $K_{D1}$-value was observed for 4e$^-$9D. An approximately 4-fold increase in $K_{D1}$ per methylene group was observed upon shortening the acyl chain from 18:0 to 16:0. This decrease in equilibrium binding affinity dependent on acyl chain length matched the ~4-fold decrease in $k_{cat}/K_M$-value per methylene group previously determined for the same substrates (Haas, J. A. and Fox, B. G. (1999) *Biochemistry*, 38, 18344–18340). This Example demonstrates that the labeled ACPs disclosed herein can be used to investigate reactions involving or mediated by ACPs.

Reagents and Proteins: Recombinant *E. coli* ACP and castor $\Delta$9D were expressed, purified, and characterized as previously described (Haas, J. A., Frederick, M. A., and Fox, B. G. (2000) *Protein Expression Purif.* 20, 274–284; Hoffman, B. J., Broadwater, J. A., Johnson, P., Harper, J., Fox, B. G., and Kenealy, W. R. (1995) *Protein Expression Purif.* 6, 646–654).

Fluoresceinylation Reaction: AminoTyr71-apo-ACP was produced as previously described in Example 6 for dansyl-ACP. The fluoresceinylation reaction was performed at 20° C. and contained 40 $\mu$M aminoTyr-ACP (~35–40 mg) in 50 mM sodium acetate, pH 5.0, with 35% (v/v) dimethyl formamide. Fluorescein isothiocyanate (Molecular Probes, Eugene, Oreg.) was prepared as a 15 mM solution in dimethyl formamide and was slowly added to the rapidly stirred reaction mixture to give a final concentration of 1.5 mM. The reaction was terminated after 1 h by the addition of aminotyrosine in 50 mM sodium acetate buffer, pH 5.0, to give a final concentration of 50 µM aminotyrosine. The fACP was precipitated by the addition of dilute acetic acid to give a pH of ~3.9, and recovered by centrifugation. The resulting protein pellet was resuspended in 8 mL of 0.3 M MES, pH 6.1. Fluoresceinyl-aminotyrosine was removed from fACP by gel filtration on a Sephadex G-15 (Pharmacia LKB Biotechnology Inc.) column (25 nm i.d.×7.5 mm bed height) equilibrated with 25 mM MES, pH 6.0, containing 0.15 M NaCl at a linear flow rate of ~12 cm/h. The column eluate containing fACP was diluted with 25 mM MES, pH 6.0, to reduce the salt concentration to 0.05 M NaCl. The fACP was further purified from difluoresceinyl-ACP on a 16/10 HiLoad Q Sepharose Fast Flow column (Pharmacia LKB Biotechnology Inc.). The column was loaded with fACP at a linear flow rate of 15 cm/h in 25 mM MES, pH 6.0, washed with 100 mL of the 25 mM MES, pH 6.0, and then washed with 100 mL of 25 mM MES, pH 6.0, containing 0.1 M NaCl. The protein was eluted at a linear flow rate of 15 cm×h$^{-1}$ in a 300 mL linear gradient from 0.05 to 0.7 M NaCl in 25 mM MES, pH 6.0. The purified fACP was characterized by electrospray ionization mass spectrometry (8913 Da expected, 8912 Da observed).

Phosphopantetheinylation, Acylation, and Characterization of Acyl-fACP: In vitro phosphopantetheinylation and acylation were carried out as previously described in Example 7 to produce acyl-fACPs in high yield (>98%, starting from apo-fACP). Acyl-fACPs were hydrolyzed at alkaline pH and the resulting free thiol in holo-fACP was quantitated with DTNB. Because the acylation reaction proceeded in high yield, the acyl-fACPs could also be quantitated by absorbance spectroscopy using the chromophore introduced by fluorescein {$\epsilon_{494}$=73,000 M$^{-1}$ cm$^{-1}$}. The concentrations of acyl-fACP determined by either the acyl-chain cleavage/DTNB reaction or by using the fluorescein molar absorptivity were within experimental error of each other.

Fluorescence Anisotropy Measurements: Fluorescence anisotropy measurements using 18:0-dACP were made on an OLIS-RSM 1000F spectrophotometer that was modified for the measurement of fluorescence anisotropy in T-format. Each photomultiplier tube was fitted with a glass long-pass 500 nm cutoff filter (Oriel, Stratford, Conn.) and either a vertical or a horizontal quartz polarizer. A 450 W Xe-arc lamp with a single grating monochrometer was used for excitation of 18:0-dACP with 335 nm light. Separate aliquots were prepared for each titration data point by diluting the 18:0-dACP to the desired final concentration in a total volume of 650 µL of 50 mM Hepes, pH 7.8, containing 35 mM NaCl. An appropriate amount of resting Δ9D was added to each aliquot of 18:0-dACP to give the desired final concentration of Δ9D with less than a 5% increase in volume for each aliquot. The final concentration of 18:0-dACP was 0.85 µM. Fluorescence anisotropy titration measurements using fACP were carried out with a Beacon 2000 Variable Temperature Fluorescence Polarization system (PanVera Corp., Madison, Wis.). Separate samples of n:0-fACP for each concentration of Δ9D were prepared as described above for 18:0-dACP, except that the final volume was 150 µL, and the final concentration of n:0-fACP was ~1 nM. Either NaCl or Fd were added to the titration buffer to give final concentrations of either 0.2 M or 3 µM, respectively.

Preparation of Samples Containing 4e$^-$Δ9D: Fluorescence anisotropy measurements using fACP and 4e$^-$Δ9D were performed in sample tubes fitted with a rubber septum stopper. Each stoppered sample was prepared with 1 mM n:0-fACP in 50 mM Hepes, pH 7.8, containing 35 mM NaCl and made anaerobic by repeated cycling between vacuum and back-fill with O$_2$-free Ar. An appropriate amount of 4e$^-$Δ9D was transferred under Ar to each aliquot of n:0-fACP to give the desired final concentration of Δ9D. The 4e$^-$Δ9D was prepared from a solution containing 32 µM resting Δ9D and 2 µM Fd in 50 mM Hepes, pH 7.8, containing 35 mM NaCl. This solution was made anaerobic by repeated cycling between vacuum and back-fill with O$_2$-free Ar. The resting Δ9D was reduced by titration with 0.15 M sodium dithionite prepared in anaerobic 1 M potassium phosphate buffer, pH 7.0, using Fd as the electron transfer mediator. Following reduction, the solution was serially diluted into anaerobic buffer under Ar to produce stock solutions containing either 3.2 µM, 0.32 µM, or 0.032 µM 4e$^-$Δ9D.

Equilibrium Fluorescence Anisotropy Measurements: In each anisotropy measurement, the intensity of the parallel and perpendicular emission from a blank containing buffer and either resting or 4e$^-$Δ9D as appropriate was subtracted from the corresponding intensity obtained from each sample. The instrument was set to read six cycles, corresponding to an integration time of 16 s per measurement. Anisotropy measurements were repeated five times for each sample, and the resulting values were averaged. The anisotropy was calculated by the Beacon software using equation 1.

$$r = \frac{(r_\parallel - r_\perp)}{(r_\perp + 2r_\parallel)} \quad (1)$$

Analysis of Equilibrium Binding Data: The data from equilibrium binding titrations of ~1 nM n:0-fACPs were analyzed by non-linear least squares fitting using Kaleidagraph (Synergy Software, West Palm Beach, Fla.) and equation 3, which provides for two independent classes of binding sites.

$$r = \frac{(r_{bound_1} - r_{free}) \times [\Delta 9D_{tot}]}{K_{D1} + [\Delta 9D_{tot}]} + \frac{(r_{bound_2} - r_{free}) \times [\Delta 9D_{tot}]}{K_{non} + [\Delta 9D_{tot}]} + r_{free} \quad (2)$$

In equation 2, r is the observed anisotropy, $r_{free}$ is the anisotropy value of either free apo- or free acyl-fACP, $K_{D1}$ is the dissociation constant for complex formation in the nM concentration range, $r_{bound_1}$ is the anisotropy value of n:0-fACP to a Δ9D subunit in the nM concentration range, $K_{non}$ is the dissociation constant for a non-specific complex formation in the ~50 µM concentration range, and $r_{bound_2}$ is the anisotropy value observed for the non-specific complex. For all titration experiments, the concentration of n:0-fACP was at least 10-fold lower than $K_{D1}$. The free concentration of Δ9D at saturation of 16:0-fACP (the least tightly bound substrate, see below) was ill-defined due to an ~10-fold difference between the saturation concentration for specific binding and the onset of binding associated with $K_{non}$. Correction of the total Δ9D concentration for the fraction bound to 18:0-fACP resulted in changes to the $K_{D1}$-values that were within error from those derived from fitting the uncorrected total Δ9D concentration data.

Therefore, $K_{D1}$-values reported are for fits to the change in anisotropy of n:0-fACP versus total Δ9D concentration.

The data from titrations of 850 nM 18:0-dACP were initially analyzed by non-linear least squares fitting and equation 2, which provides the analytical solution for stoichiometric binding:

$$r = r\max(A + E + K_{D2} - \sqrt{((A + E + K_{D2})^2 + 4AE)})2E \quad (3)$$

where $V_{max}$ is from steady-state kinetic measurements, A is #, E is the free concentration of enzyme during the progress of the titration, and $K_{D2}$ is the desired dissociation constant for complex formation in the 100–200 nM concentration range.

For evaluation of the simultaneous contribution of two binding equilibria during the titration experiments, the Nsolve routine (Mathematica 4.0.1.0, Wolfram Research, Inc., Champaign, Ill.) was used to calculate the individual concentrations of all enzyme and substrate species present during the progress of the titration experiments. These concentrations were used to calculate predicted anisotropy values using the end-point anisotropy values of 0.11 for unbound acyl-dACP and 0.223 for the acyl-dACP-Δ9D complex obtained from titration experiments.

Time-Resolved Fluorescence Anisotropy Measurements: These measurements were made with an SX. 18M stopped-flow spectrophotometer equipped with an FP. 1 fluorescence polarization modification (Applied Photophysics, Leatherhead, United Kingdom). The instrument was configured in T-format and emission was collected through Schott OG-530 glass cutoff filters (Oriel) placed in front of each photomultiplier tube. To determine $k_{off}$ from Δ9D for each of the n:0-fACPs, syringe 1 was loaded with 0.2 μM n:0-fACP and 2 μM Δ9D that had been allowed to equilibrate for 5 min at 23° C. in 50 mM Hepes, pH 7.8, containing 35 mM NaCl. Syringe 2 was loaded with either buffer (control experiment) or with 20 μM 18.0-ACP that was not labeled with fluorescein (competition binding experiment). Following mixing, the final concentrations in the flow cell were 0.1 μM n:0-fACP, 1 μM Δ9D, and when present, 10 μM 18:0-ACP. Data were collected in an oversampling mode with 1000 points collected per shot. For each n:0-fACP, the data from five consecutive shots were averaged and smoothed using software provided with the instrument. The data were fit to a single exponential decay with the Levenberg-Marquardt algorithm provided in Kaleidagraph. The errors for $k_{off}$ values were derived from the fitting procedures.

Figure 7A:
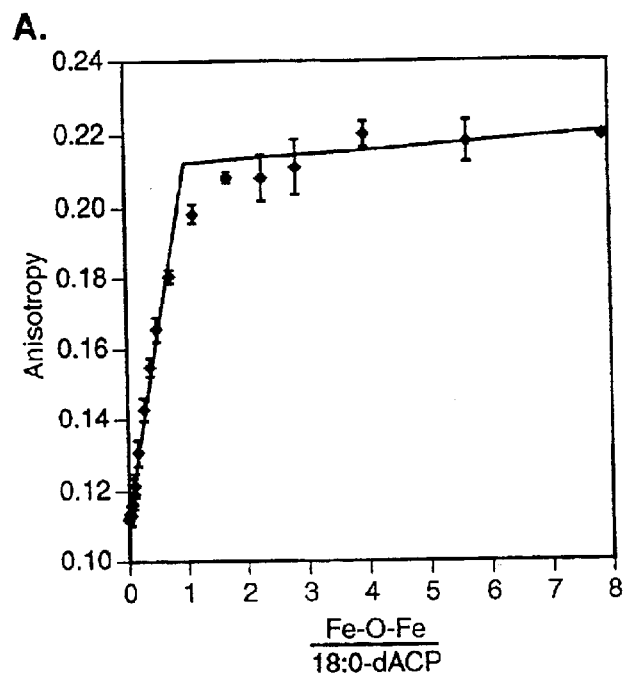
FIGS. 7A and 7B.
Figure 7B:
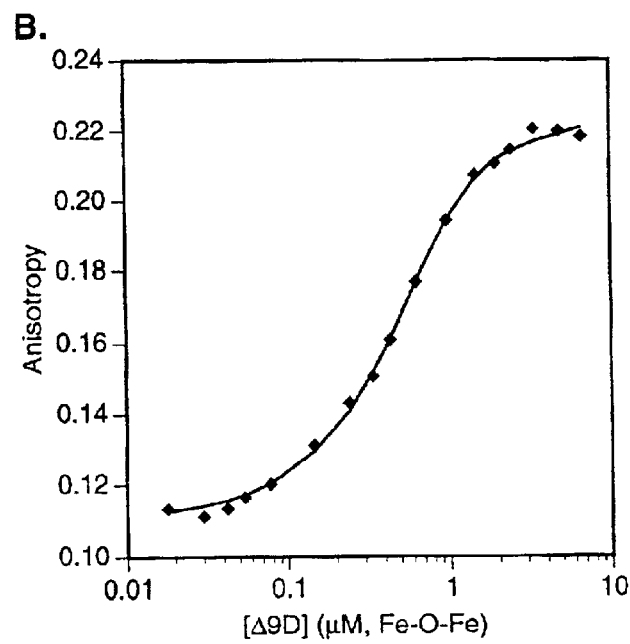

Binding Interactions with Dansyl-18:0-ACP: In this Example, 18:0-dACP showed no fluorescence quenching in the presence of resting Δ9D. This result was consistent with the intentional attachment of the fluorophore near to the C-terminal of ACP so as to not interfere with productive binding or catalysis. Titration of 18:0-dACP with Δ9D showed stoichiometric binding of 18:0-dACP relative to Δ9D active sites at less than JIM concentrations (FIG. 7A). Non-linear least squares fitting using equation 2 gave a $K_D$-value of 136 nM for the interaction of 850 nM 18:0-dACP with increasing concentrations of Δ9D (FIG. 7B). These experiments also established 850 nM to be the lower effective concentration for $K_D$ determinations using 18:0-dACP due to the diminishing fluorescence intensity observed from dACP. Thus a fluorophore with increased quantum yield was required in order to extend the effective concentration for the titrations to the low nM concentration range so that further investigation of the equilibrium distribution between free and bound species could be undertaken.

Catalytic Efficacy of Acyl-Fluoresceinyl-ACPs: fACP was synthesized on the milligram scale (yield of fACP >25% relative to starting apo-ACP), phosphopantetheinylated, and acylated. Steady state kinetic characterizations revealed $k_{cat}$=20 min$^{-1}$ and $K_M$=2.2 μM for desaturation of 18:0-fACP to 18:1-fACP. These values were nearly identical to those determined previously for 18:0-fACP and 18:0-dACP (Haas, J. A., Frederick, M. A., and Fox, B. G. (2000) *Protein Expression Purif.* 20, 274–284). Furthermore, the $k_{cat}/K_M$=9 μM$^{-1}$ min$^{-1}$ determined for 18:0-fACP was close to the 10 μM$^{-1}$ min$^{-1}$ previously reported for 18:0-ACP[11]. These results establish the efficacy of 18:0-fACP as a catalytically silent probe for study of binding with Δ9D.

Figure 8A:
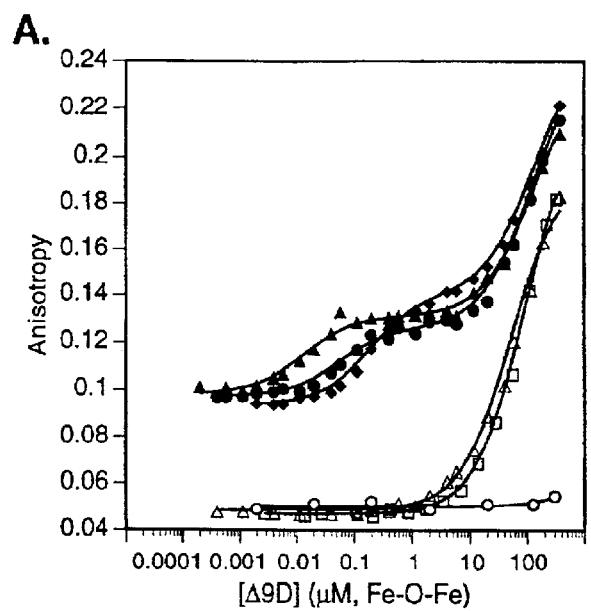
FIGS. 8A and 8B: Fluorescence anisotropy change during titration of FIG. 8A: 1 nM 18:0-fACP (▲), 0.7 nM 17:0-fACP (●), 1.3 nM 16:0-fACP (♦), 0.97 nM apo-fACP with Δ9D (Δ), 0.97 nM apo-fACP with lysozyme (□), or 0.97 nM apo-fACP with T4moD (○).
Figure 8B:
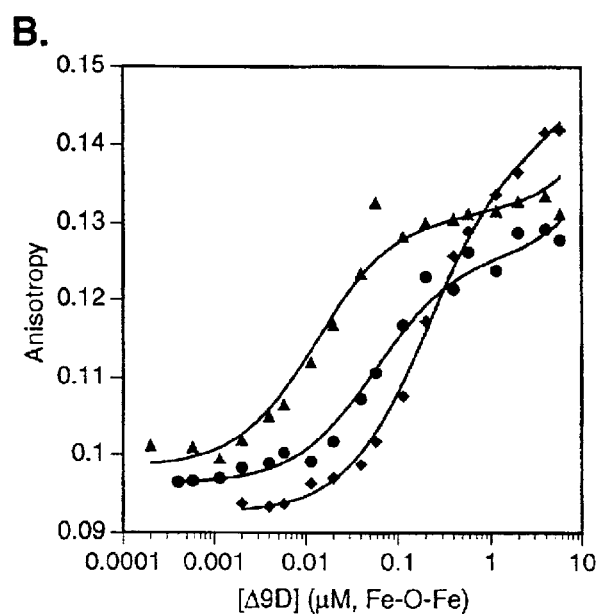

Binding Interactions with Acyl-fACP: FIGS. 8A and 8B (solid symbols) shows fluorescence anisotropy data obtained during the titration of 16:0-, 17:0-, and 18:0-fACP with resting Δ9D. As indicated by the two inflections in FIG. 8A, two separate binding events were observed for each of these substrates. The first binding event (assigned as $K_{D1}$) occurred in the nM concentration range and was dependent upon the acyl chain length (FIG. 8B). This result implicated the presence of an acyl chain in the formation of a high affinity complex with resting Δ9D. By consideration of mass balance, all n:0-ACP present in the titration mixture was bound by completion of this first binding event. The second binding event was observed when the concentration of Δ9D added exceeded ~5 μM. This second binding event was independent of acyl chain length as titration of apo-fACP with Δ9D (FIG. 8A, open squares) gave no change in anisotropy when Δ9D was in the nM concentration range, whereas a change in anisotropy comparable to that obtained with 18:0-ACP was detected when the concentration of Δ9D exceeded ~5 μM. Because mass balance considerations demanded that only bound fACP was present when the concentration of Δ9D was ~100 nM or higher, the anisotropy changes detected for concentrations of Δ9D above ~5 μM must represent non-specific interactions between the already-formed 18:0-fACP-Δ9D complex and excess Δ9D.

Acyl-Chain Length Dependence of Equilibrium Dissociation Constants: FIG. 8B shows the anisotropy data obtained from titrations of 16:0-, 17:0-, and 18:0-fACP using resting Δ9D in the nM concentration range. The solid lines are the result of non-linear least squares fitting using the two binding site model of equation 3. The results show that for each methylene group added to an acyl chain of length 16:0 to 18:0, an approximate 4-fold increase in the affinity of the complex with resting Δ9D was obtained. The $K_D$-value measured by titration of 1 nM 18:0-fACP with Δ9D (now defined to be $K_{D1}$=13 nM) represents a distinct, approximately 10-fold tighter binding event than the $K_D$-value represented by titration of 850 nM 18:0-dACP with Δ9D (now defined to be $K_{D2}$=170 nM). The ability to measure these two different $K_D$-values has arisen in part from the difference in fluorescence quantum yield for the two probes utilized, which allowed similar experiments to be performed in concentration regimes differing by 850-fold.

For studies of 18:0-fACP binding to 4e$^-$Δ9D, an O$_2$-free preparation of resting Δ9D was first reduced in the presence of a substoichiometric amount of Fd as the redox mediator and sodium dithionite as the reductive titrant. The reduction was monitored by optical spectroscopy at 350 nm, and indicated that greater than 95% reduction of the diiron centers was achieved. A titration of O$_2$-free 18:0-fACP using these preparations of 4e$^-$Δ9D gave a $K_{D1}$-value indistinguishable from that measured for the complex with resting Δ9D (data not shown). This result suggested that major changes in the affinity for other acyl-ACPs would not be produced as result of redox transformations of the Δ9D duron center. Therefore, further investigation of the binding interactions with 4e$^-$Δ9D were not undertaken.

Determination of Dissociation Rate Constants: Due to the higher detection limit required for stopped-flow experiments (~100 nM acyl-fACP) and the concentration of unlabled 18:0-ACP required for effective competition (10 μM), these experiments primarily access the dissociation rate constant contributing to $K_{D2}$. FIG. 3 shows the time-dependent anisotropy changes resulting from the dissociation of 16:0-, 17:0-, and 18:0-fACP from Δ9D. The results from control experiments where the corresponding preformed acyl-fACP•Δ9D complexes were mixed with buffer are also shown in FIG. 3. For each acyl-fACP, a rapid decrease in anisotropy was observed upon mixing of the complex with unlabeled 18:0-ACP, corresponding to the displacement of the bound fluorophore by the unlabeled substrate. In each case, the data were well-fitted by a single exponential decay as judged by plotting residuals for the fits (FIG. 3). The dissociation rate constants (herein defined to be $k_d$) calculated for the various acyl-fACPs from these fits are given in Table 1. An increase in dissociation rate was observed as the length of the acyl-chain attached to fACP was shortened, with an ~130-fold increase in dissociation rate for 16:0-fACP as compared to 18:0-fACP. Furthermore, the end-point anisotropy observed after the stopped-flow mixed solution had reached equilibrium was lower for 16:0-fACP relative to 17:0-or more noticeably, 18:0-fACP. This difference in amplitude reflected the ability of the unlabeled 18:0-ACP to more effectively compete against the less tightly bound 16:0- and 17:0-ACPs than the more tightly bound 18:0-fACP.

Electrostatics of Acyl-ACP and Resting Δ9D Binding: ACP is an acidic molecule, with a net negative surface charge in solution at neutral pH. Lysozyme (11.4 kDa, pI>7) and T4moD (11.6 kDa, pI<7) were used to further investigate the origin of the changes in fACP anisotropy observed when Δ9D was added in the $\mu$M protein concentration range. These two proteins have approximately the same molecular mass (and thus will likely give similar contributions to solution viscosity at similar protein concentrations). However, due to the difference in pI values, these two proteins will have substantially different net charge at the pH of the binding experiments. Titration of apo-fACP with lysozyme (FIG. 8A, open square symbols) produced no change in anisotropy in the nM concentration range but gave a substantial change in anisotropy in the $\mu$M concentration range. In contrast, titration of apo-fACP with T4moD produced only a small anisotropy change (r≈0.005) over the entire concentration range used (FIG. 8A, open circle symbols). These results suggest that the anisotropy changes observed from fACP in the presence of lysozyme arise from an electrostatic interaction. Because Δ9D also has substantial number of positively charged amino acid residues on the surface, the binding equilibrium observed at Δ9D concentrations of ~5 $\mu$M and above also likely arises from electrostatic interactions.

Figure 9:
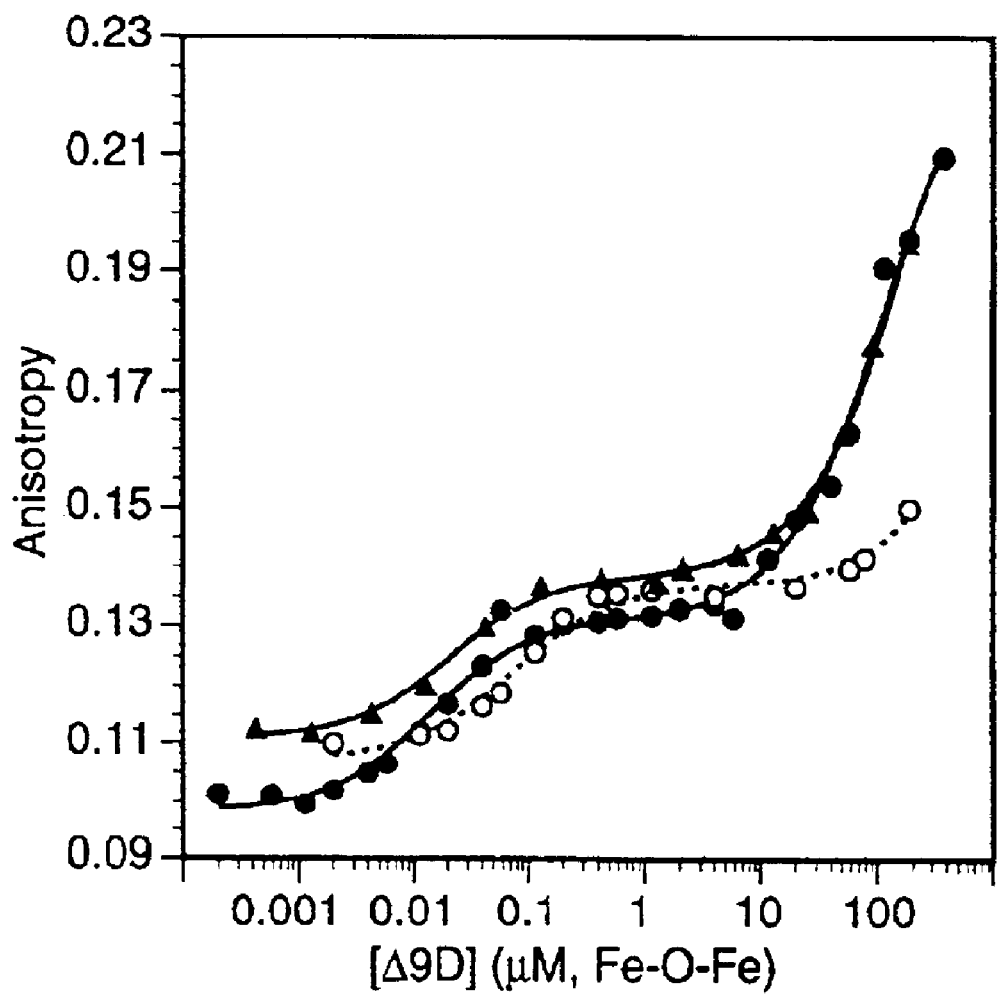
FIG. 9: Changes in fluorescence anisotropy due to titration of 1 nM 18:0-fACP with Δ9D at pH 7.8 in the presence of (▲) 0.035 M NaCl, (•), 3 µM {2Fe-2S} Fd, and (○) 0.2 M NaCl. Solid and dotted lines are the results of non-linear least squares fitting performed as in FIG. 8B.

Effect of {2Fe-2S} Ferredoxin or Ionic Strength on Acyl-ACP and Resting Δ9D Binding: FIG. 9 shows that inclusion of oxidized Fd (solid circle symbols) in the titration buffer at the same concentration used for steady-state kinetic analysis (3 $\mu$M) had no effect on $K_{D1}$ determined by titration of 18:0-fACP with Δ9D in the nM concentration range. Furthermore, the inclusion of Fd did not change the nature of the non-specific binding interaction observed when the Δ9D concentration was greater than ~5 $\mu$M. FIG. 9 also shows that the binding affinity of 18:0-fACP for Δ9D in the presence of 0.2 M NaCl was decreased ~5 fold in the nM concentration range ($K_{D1}$=37±7.7 nM), while the change in anisotropy assigned to non-specific electrostatic interactions was nearly completely eliminated ($K_{non}$>500 $\mu$M). When steady-state kinetic measurements were performed in an assay buffer modified to include 0.2 M NaCl, only a slight change in $k_{cat}$ was observed (0.65 s$^{-1}$) relative to the assay buffer containing 35 mM NaCl (0.60 s$^{-1}$), implying that the tightly bound forms associated with $K_{D1}$ and $K_{D2}$ (forms present at the Δ9D and n:0-ACP concentrations of the assay) are those relevant to the initation of catalysis. Furthermore, these results support the fundamental importance of the acyl chain (hydrophobic) interactions in forming a tight complex with resting Δ9D.

Bibliography

1. Magnuson, K., Jackowski, S., Rock, C. O. & Cronan, J. E., Jr. (1993). Regulation of fatty acid biosynthesis in *Escherichia coli*. *Annu. Rev Microbiol*. 57, 522–542.
2. Rusnak, F., Sakaitani, M., Drucckhammer, D., Reichert, J. & Walsh, C. T. (1991). Biosynthesis of the *Escherichia coli* siderophore enterobactin: Sequence of the entF gene, expression and purification of EntF, and analysis of covalent phosphopantetheine. *Biochemistry* 30, 2916–2927.
3. Baldwin, J. E., Bird, J. W., Field, R. A., O'Callaghan, N. M., Schofield, C. J. & Willis, A. C. (1991). Isolation and partial characterisation of ACV synthetase from *Cephalosporium acremonium* and *Streptomyces clavuligerus*: Evidence for the presence of phosphopantothenate in ACV synthetase. *J. Antibiot*. (Tokyo) 44, 241–248.
4. Summers, R. G., Ali, A., Shen, B., Wessel, W. A. & Hutchinson, C. R. (1995). Malonyl-coenzyme A:acyl carrier protein acyl-transferase of *Streptomyces glaucescens*: A possible link between fatty acid and polyketide biosynthesis. *Biochemistry* 34, 9389–9402.
5. Lawson, D. M., Derewenda, U., Serre, L. Ferri, S., Szittner, R., Wei, Y., Meighan, E. A. & Derewenda, Z. S. (1994). Structure of a myristoyl-ACP-specific thioesterase from *Vibrio harveyi*. *Biochemistry* 33, 9382–9388.
6. Shanklin, J. & Cahoon, E. B. (1998). Desaturation and related modifications of fatty acids. *Annu. Rev. Plant Physiol. Plant Mol. Biol*. 49, 611–641.
7. Fox, B. G. (1997). Catalysis by non-heme iron. In *Comprehensive Biological Catalysis* (Sinnott, M., ed.), pp. 261–348. Academic Press, London.
8. Fox, B. G., Shanklin, J., Somerville, C. & Munck, E. (1993). Stearoyl-acyl carrier protein ΔD$^9$ desaturase from *Ricinus communis* is a diiron-oxo protein. *Proc. Natl. Acad Sci*., USA 90, 2486–2490.
9. Fox, B. G., Shanklin, J., Ai, J., Loehr, T. M. & Sanders-Loehr, J. (1994). Resonance Raman evidence for an Fe—O—Fe center in stearoyl-ACP desaturase. Primary sequence identity with other diiron-oxo proteins. *Biochemistry* 43, 12776–12786.
10. Lindqvist, Y., Huang, W., Schneider, G. & Shanklin, J. (1996). Crystal structure of stearoyl-acyl carrier protein Δ$^9$ desaturase from castor seed and its relationship to other diiron proteins. *EMBO J*. 15, 4081–4092.
11. Haas, J. A. & Fox, B. G. (1999). Role of hydrophobic partitioning in substrate selectivity and turnover of the *Ricinus communis* stearoyl-ACP Δ$^9$ desaturase. *Biochemistry* 38, 12833–12840.
12. Yang, Y., Broadwater, J. A., Pulver, S. C., Fox, B. G. & Solomon, E. I. (1999). Circular dichroism and magnetic circular dichroism studies of the reduced binuclear non-heme iron site of stearoyl-ACP Δ$^9$ desaturase: substrate binding and comparison to ribonucleotide reductase. *J. Am. Chem. Soc*. 121, 2770–2783.
13. Broadwater, J. A., Ai, J., Loehr, T. M., Sanders-Loehr, J. & Fox, B. G. (1998). Peroxodiferric intermediate of stearoyl-acyl carrier protein Δ$^9$ desaturase: oxidase reactivity during single turnover and implications for the mechanism of desaturation. *Biochemistry* 37, 14664–14671.
14. Broadwater, J. A., Achirm, C., Munck, E. & Fox, B. G. (1999). Mössbauer studies of the formation and reactivity of a quasi-stable peroxo intermediate of stearoyl-acyl carrier protein $\Delta^9$-desaturase. *Biochemistry* 38, 12197–12204.
15. Broadwater, J. A. & Fox, B. G. (1999). Spinach holo-acyl carrier protein: overproduction and phosphopantetheinylation in *Escherichia coli* BL21 (DE3), in vitro acylation, and enzymatic desaturation of histidine-tagged isoform I. *Protein Express. Purif.* 15, 314–326.
16. Sambrook, J., Fritsch, E. F. & Maniatis, T., Eds. (1989). *Molecular Cloning. A Laboratory Manual.* 2nd edit. Cold Spring Harbor Laboratory Press, Cold Spring Harbor, N.Y.
17. Studts, J. M. & Fox, B. G. (1999). Application of fed-batch fermentation to the preparation of isotopically labeled or selenomethionyl-labeled proteins. *Protein Express. Purif.* 16, 109–119.
18. Schagger, H. & von Jagow, G. (1987). Tricine-sodium dodecyl sulfate-polyacrylamide gel eletrophoresis for the separation of proteins in the range from 1 to 100 kDa. *Anal. Biochem.* 166, 368–379.
19. Ellman, G. L. (1959). Tissue sulfhydryl groups. *Arch. Biochem. Biophys.* 82, 70–77.
20. Hill, R. B., MacKenzie, K. R., Flanagan, J. M., Cronan, J. E. & Prestegard, J. H. (1995). Overexpression, purification, and characterization of *Escherichia coli* acyl carrier protein and two mutant proteins. *Protein Express. Purif.* 6, 394–400.
21. Sokolovsky, M., Riordan, J. F. & Vallee, B. L. (1966). Tetranitromethane. A reagent for the nitration of tyrosyl residues in proteins. Biochemistry 5, 3582–3588.
22. Kenner, A. (1971). Fluorescent derivatives of nitrotyrosine. Model compounds for fluorescent reporter groups in proteins. *Biochemistry* 10, 545–550.
23. Rock, C. O. & Gan in, J. L. (1979). Preparative enzymatic synthesis and hydrophobic chromatography of acyl-acyl carrier protein. *J. Biol. Chem.* 254, 7123–7128.
24. Keating, D. H., Carey, M. R. & Cronan, J. E., Jr. (1995). The unmodified (apo) form of *Escherichia coli* acyl carrier protein is a potent inhibitor of cell growth. *J. Biol. Chem.* 270, 22229–22235.
25. Aristidou, A. A., San, K. & Bennett, G. N. (1999). Improvement of biomass yield and recombinant gene expression in *Escherichia coli* by using fructose as the primary carbon source. *Biotechnol. Prog.* 15, 140–145.
26. Prescott- D. J. & Vagelos, P. R. (1972). Acyl carrier protein. *Adv. Enzy. and Rel. Areas of Mol. Bio.* 36, 269–311.
27. Sokolovsky, M., Riordan, J. F. & Vallee, B. L. (1967). Conversion of 3-nitrotyrosine to 3-aminotyrosine in peptides and proteins. *Biochem. Biophys. Res. Commun.* 27, 20–25.
28. Abita, J. P., Lazdunski, M. & Ailhaud, G. (1971). Structure-function relationships of the acyl-carrier protein of *Escherichia coli. Eur. J. Biochem* 23, 412–420.
29. Bradford, M. M. (1976). A rapid and sensitive method for the quantitation of microgram quantities of protein utilizing the principle of protein-dye binding. *Anal Biochem.* 72, 248–254.
30. Kraulis; P. J. (1991). MOLSCRIPT: a program to produce both detailed and schematic plots of protein structures. *J. Appl. Crystal.* 24, 946–950.
31. Kim, Y. & Prestegard, J. B. (1990). Refinement of the NMR structures for acyl carrier protein with scalar coupling data. *Proteins: Struct. Funct. Genet.* 8, 377–385.
32. Miller, M. B., and Bassler; B. L. (2001), Annual Review of Microbiology. 55, 165–199.
33. Hoang, T. T., Ma, Y., Stem, R. J., McNeil, M. R., and Schweizer, H. P. (1999) *Gene* 237, 361–371.
34. Singh, P. K., Schaefer, A. L., Parsek, M. R., Moninger, T. O., Welsh, M. J., and Greenberg, E. P. (2000) "The Establishment of Biofilms." *Nature* 407, 762–764.
35. Garsin, D. A., Sifri, C. D., Myolankis, E., Qin, X., Singh, K. V., Murray, B. E., Calderwood, S. B., and Ausubel, F. M. (2001) *Proceedings of the National Academy of Sciences USA* 98, 10892–10897.
36. Sperandio, V., Torres, Giron, J. A., and Kaper, J. B. (2001) *Journal of Bacteriology* 183, 5187–5197).

What is claimed is:

1. A labeled acyl carrier protein comprising: an acyl carrier protein having at least one tyrosine residue, and a non-radioactive label bonded to the at least one tyrosine residue wherein the non-radioactive label is a fluorophore.

2. The labeled acyl carrier protein of claim 1, wherein the acyl carrier protein is an apo-acyl carrier protein.

3. The labeled acyl carrier protein of claim 1, wherein the acyl carrier protein is a holo-acyl carrier protein.

4. The labeled acyl carrier protein of claim 1, wherein the acyl carrier protein is an acylated-acyl carrier protein.

5. The labeled acyl carrier protein of claim 1, wherein the acyl carrier protein is derived from *E. coli*.

6. The labeled acyl carrier protein of claim 1, wherein the fluorophore is selected from the group consisting of dansyl, fluorescein, rhodamine, fluorescein isothiocyanate, tetramethylrhodamine isothiocyanate, and Texas Red.

7. The labeled acyl carrier protein of claim 1, wherein the fluorophore is selected from the group consisting of dansyl and fluorescein.

8. A labeled acyl carrier protein comprising: an acyl carrier protein having one and no more than one tyrosine residue; the tyrosine residue being modified to include a fluorophore covalently bonded thereto.

9. The labeled acyl carrier protein of claim 8, wherein the acyl carrier protein is an apo-acyl carrier protein.

10. The labeled acyl carrier protein of claim 8, wherein the acyl carrier protein is a holo-acyl carrier protein.

11. The labeled acyl carrier protein of claim 8, wherein the acyl carrier protein is an acylated-acyl carrier protein.

12. The labeled acyl carrier protein of claim 8, wherein the acyl carrier protein is derived from *E. coli*.

13. The labeled acyl carrier protein of claim 8, wherein the fluorophore is selected from the group consisting of dansyl, fluorescein, rhodamine, fluorescein isothiocyanate, tetramethylrhodamine isothiocyanate, and Texas Red.

14. The labeled acyl carrier protein of claim 8, wherein the fluorophore is selected from the group consisting of dansyl and fluorescein.

15. A kit for investigating reactions involving acyl carrier proteins, the kit comprising a container having disposed therein an acyl carrier protein having at least one tyrosine residue, and a non-radioactive label covalently bonded to the at least one tyrosine residue, wherein the non-radioactive label is a fluorophore.

16. The kit of claim 15, wherein the acyl carrier protein has no more than one tyrosine residue.

17. The kit of claim 15, wherein the acyl carrier protein is an apo-acyl carrier protein.

18. The kit of claim 15, wherein the acyl carrier protein is a holo-acyl carrier protein.

19. The kit of claim 15, wherein the acyl carrier protein is an acylated-acyl carrier protein.

20. The kit of claim 15, wherein the acyl carrier protein is derived from *E. coli*.

21. The kit of claim 15, wherein the fluorophore is selected from the group consisting of dansyl, fluorescein, rhodamine, fluorescein isothiocyanate, tetramethylrhodamine isothiocyanate, and Texas Red.

22. The kit of claim 15, wherein the fluorophore is selected from the group consisting of dansyl and fluorescein.

23. A method of making a holo-acyl carrier protein having a non-radioactive label affixed thereto, the method comprising:

(a) reacting an apo-acyl carrier protein having at least one tyrosine residue with a chemical reagent capable of covalently bonding an amino moiety to the tyrosine residue, to thereby yield an apo-acyl carrier protein having an amino-modified tyrosine moiety; then (b) covalently bonding a non-radioactive label to the amino-modified tyrosine moiety of step (a), thereby to yield an apo-acyl carrier protein having a non-radioactive label covalently bonded thereto; and then (c) reacting the apo-acyl carrier protein of step (b) with a holo-acyl carrier protein synthase under time and conditions sufficient to convert the apo-acyl carrier protein to a holo-acyl carrier protein having a non-radioactive label affixed thereto.

24. A method of making an acylated-acyl carrier protein having a non-radioactive label affixed thereto, the method comprising:

(a) reacting an apo-acyl carrier protein having at least one tyrosine residue with a chemical reagent capable of covalently bonding an amino moiety to the tyrosine residue, to thereby yield an apo-acyl carrier protein having an amino- modified tyrosine moiety; then (b) covalently bonding a non-radioactive label to the amino-modified tyrosine moiety of step (a), thereby to yield an apo-acyl carrier protein having a non-radioactive label covalently bonded thereto; then (c) reacting the apo-acyl carrier protein of step (b) with a holo-acyl carrier protein synthase under time and conditions sufficient to convert the apo-acyl carrier protein to a holo-acyl carrier protein having a non-radioactive label affixed thereto; and then (d) reacting the holo-acyl carrier protein of step (c) with an acyl-ACP synthetase under time and conditions sufficient to convert the holo-acyl carrier protein to an acylated acyl carrier protein having a non-radioactive label affixed thereto.

25. A labeled acyl carrier protein comprising:

an acyl carrier protein derived from *E. coil* and having at least one tyrosine residue, wherein the acyl carrier protein is selected from the group consisting of apo-acyl carrier proteins, holo-acyl carrier proteins, and acylated-acyl carrier protein; and a fluorophore covalently bonded to the at least one tyrosine residue of the acyl carrier protein.

26. The labeled acyl carrier protein of claim 25, wherein the fluorophore is selected from the group consisting of dansyl, fluorescein, rhodamine, fluorescein isothiocyanate, tetramethylrhodamine isothiocyanate, and Texas Red.

27. The labeled acyl carrier protein of claim 25, wherein:

the fluorophore is dansyl; and the fluorophore is covalently bonded to the at least one tyrosine residue via an amino moiety.

28. A labeled acyl carrier protein comprising:

an acyl carrier protein having at least one tyrosine residue, wherein the acyl carrier protein is selected from the group consisting of apo-acyl carrier proteins, holo-acyl carrier proteins, and acylated-acyl carrier protein;

an o-amino moiety bonded to the at least one tyrosine residue; and a non-radioactive label covalently bonded to the at least one tyrosine residue of the acyl carrier protein via the o-amino moiety.

29. The labeled acyl carrier protein of claim 28, wherein the acyl carrier protein is derived from *E. coli*, and the non-radioactive label is selected from the group consisting of dansyl, fluorescein, rhodamine, fluorescein isothiocyanate, tetramethylrhodamine isothiocyanate, and Texas Red.

30. A kit for investigating reactions involving acyl carrier proteins, the kit comprising:
- a container having disposed therein an acyl carrier protein having one and no more than one tyrosine residue, wherein the acyl carrier protein is selected from the group consisting of apo-acyl carrier proteins, holo-acyl carrier proteins, and acylated-acyl carrier protein; and
- a fluorophore covalently bonded to the at least one tyrosine residue of the acyl carrier protein.

31. The kit of claim 30, wherein:

the acyl carrier protein is derived from *E. coli;* the fluorophore is selected from the group consisting of dansyl, fluorescein, rhodamine, fluorescein isothiocyanate, tetramethylrhodamine isothiocyanate, and Texas Red; and the fluorophore is covalently bonded to the one tyrosine residue via an amino moiety.

32. A kit for investigating reactions involving acyl carrier proteins, the kit comprising:
- a container having disposed therein an acyl carrier protein derived from *E. coli* and having at least one tyrosine residue, wherein the acyl carrier protein is selected from the group consisting of apo-acyl carrier proteins, holo-acyl carrier proteins, and acylated-acyl carrier protein;
- anti o-amino moiety bonded to the at least one tyrosine residue; and
- a non-radioactive label covalently bonded to the at least one tyrosine residue of the acyl carrier protein via the o-amino moiety.

33. The kit of claim 30, wherein:

the non-radioactive label is selected from the group consisting of dansyl, fluorescein, rhodamine, fluorescein isothiocyanate, tetramethylrhodamine isothiocyanate, and Texas Red; and the fluorophore is covalently bonded to the at least one tyrosine residue via an amino moiety.

34. A kit for investigating reactions involving acyl carrier proteins, the kit comprising:
- a container having disposed therein an acyl carrier protein derived from *E. coli* and having at least one tyrosine residue, wherein the acyl carrier protein is selected from the group consisting of apo-acyl carrier proteins, holo-acyl carrier proteins; and acylated-acyl carrier protein; and
- a dansyl moiety bonded to the at least one tyrosine residue.

35. A labeled acyl carrier protein comprising:

an acyl carrier protein derived from *E. coli* and having at least one tyrosine residue, wherein the acyl carrier protein is selected from the group consisting of apo-acyl carrier proteins, halo-acyl carrier proteins, and acylated-acyl carrier protein; and a dansyl moiety covalently bonded to the at least one tyrosine residue of the acyl carrier protein.

* * * * *